United States Patent
Strangeman et al.

(10) Patent No.: US 12,042,313 B2
(45) Date of Patent: Jul. 23, 2024

(54) RADIATION PROTECTION

(71) Applicant: LEO CANCER CARE, INC., Middleton, WI (US)

(72) Inventors: Mark Strangeman, West Sussex (GB); Stephen Towe, East Sussex (GB); Richard Haley, East Sussex (GB); Alexandra Adrych-Brunning, Cheshire (GB)

(73) Assignee: LEO CANCER CARE, INC., Middleton, WI (US)

( * ) Notice: Subject to any disclaimer, the term of this patent is extended or adjusted under 35 U.S.C. 154(b) by 118 days.

(21) Appl. No.: 17/680,798

(22) Filed: Feb. 25, 2022

(65) Prior Publication Data
US 2022/0304635 A1    Sep. 29, 2022

Related U.S. Application Data

(60) Provisional application No. 63/154,241, filed on Feb. 26, 2021.

(51) Int. Cl.
*A61B 6/10* (2006.01)
*A61B 6/00* (2024.01)
*A61B 6/04* (2006.01)

(52) U.S. Cl.
CPC .......... *A61B 6/107* (2013.01); *A61B 6/0407* (2013.01); *A61B 6/48* (2013.01)

(58) Field of Classification Search
CPC ......... A61B 6/0407; A61B 6/107; A61B 6/40; A61B 6/48; G21F 7/005; G21F 3/00; G21F 1/00; G21F 3/04; G21F 7/00; A61N 2005/1094
See application file for complete search history.

(56) References Cited

U.S. PATENT DOCUMENTS

| | | | |
|---|---|---|---|
| 5,937,598 A * | 8/1999 | Rain | G21F 7/03 250/517.1 |
| 5,999,836 A | 12/1999 | Nelson et al. | |
| 8,712,012 B2 | 4/2014 | O'Connor | |
| 10,531,844 B1 * | 1/2020 | Ghazi | A61B 6/032 |
| 10,878,974 B2 * | 12/2020 | Ford | G21F 3/04 |
| 2002/0101958 A1 | 8/2002 | Bertsche | |
| 2002/0166293 A1 * | 11/2002 | Zeik | E04H 3/08 52/79.1 |
| 2004/0025448 A1 * | 2/2004 | Puusepp | E04H 3/08 52/64 |

(Continued)

OTHER PUBLICATIONS

"Healthcare resource statistics—technical resources and medical terminology", Statistics Explained, Eurostat (European Union) publication accessed Sep. 24, 2020. https://ec.europa.eu/eurostat/statistics-explained/index.php?title=Healthcare_resource_statistics_-_technical_resources_and_medical_technology.

(Continued)

*Primary Examiner* — Dani Fox
*Assistant Examiner* — Soorena Kefayati
(74) *Attorney, Agent, or Firm* — Casimir Jones, S.C.; Thomas A. Isenbarger

(57) ABSTRACT

Provided herein is technology relating to controlling radiation and protecting biological organisms from exposure to radiation and particularly, but not exclusively, to apparatuses, methods, and systems for minimizing and/or eliminating exposure of humans to stray radiation used for medical imaging and therapy.

30 Claims, 10 Drawing Sheets

(56) References Cited

U.S. PATENT DOCUMENTS

| | | | |
|---|---|---|---|
| 2005/0218348 A1* | 10/2005 | Fehrenbacher | G21F 7/00 250/517.1 |
| 2007/0012888 A1* | 1/2007 | Bichay | G21F 7/00 250/496.1 |
| 2008/0203331 A1* | 8/2008 | Murphy | A61N 5/10 250/517.1 |
| 2008/0308754 A1* | 12/2008 | Fehrenbacher | G21F 3/04 250/517.1 |
| 2009/0128351 A1* | 5/2009 | Ma | A61B 6/107 340/686.1 |
| 2011/0101246 A1* | 5/2011 | Yajima | H05H 7/001 250/492.3 |
| 2011/0101254 A1* | 5/2011 | Yajima | G21K 5/04 250/515.1 |
| 2011/0142202 A1* | 6/2011 | Brown | G21K 1/10 378/65 |
| 2011/0198516 A1* | 8/2011 | Fan | G21F 7/00 250/515.1 |
| 2012/0207276 A1* | 8/2012 | Pomper | A61N 5/1001 250/492.1 |
| 2013/0047521 A1* | 2/2013 | Yoder | G21F 7/005 52/745.02 |
| 2013/0064344 A1* | 3/2013 | Carol | A61B 6/04 378/10 |
| 2013/0082196 A1* | 4/2013 | Farrell | B32B 15/18 250/496.1 |
| 2013/0175461 A1* | 7/2013 | Lambert | G21F 3/00 250/517.1 |
| 2014/0029727 A1* | 1/2014 | Ono | H01J 35/32 378/121 |
| 2015/0090894 A1* | 4/2015 | Zwart | H05H 13/02 250/396 ML |
| 2016/0016011 A1* | 1/2016 | Haruna | A61N 5/10 600/1 |
| 2016/0051844 A1* | 2/2016 | Tajiri | A61N 5/1077 250/517.1 |
| 2016/0276047 A1* | 9/2016 | Yamamoto | B41J 2/442 |
| 2016/0324490 A1* | 11/2016 | Brachman | G21F 3/00 |
| 2017/0119324 A1* | 5/2017 | Wilson | G21F 3/00 |
| 2017/0258414 A1 | 9/2017 | Guertin et al. | |
| 2018/0070912 A1* | 3/2018 | Lin | A61B 6/025 |
| 2018/0116044 A1* | 4/2018 | Radovinsky | H05H 7/04 |
| 2018/0169439 A1* | 6/2018 | Shapiro | A61N 5/1039 |
| 2018/0258659 A1* | 9/2018 | LeBlanc | E04B 7/20 |
| 2019/0142353 A1* | 5/2019 | Stegehuis | A61B 6/107 250/515.1 |
| 2020/0155869 A1* | 5/2020 | Chamberlain | B60P 3/00 |
| 2020/0268327 A1* | 8/2020 | Feain | A61B 6/0487 |
| 2021/0026023 A1 | 1/2021 | Maolinbay | |
| 2021/0290978 A1* | 9/2021 | Shinton | A61N 5/10 |
| 2021/0330990 A1* | 10/2021 | Chen | A61G 10/00 |
| 2022/0130565 A1* | 4/2022 | Lemer | G21F 7/03 |

OTHER PUBLICATIONS

Boisbouvier, S. et al. Upright patient positioning for pelvic radiotherapy treatments. Tech Innov Patient Support Radiat Oncol. Nov. 28, 2022;24:124-130.

Borras, J.M. et al. The optimal utilization proportion of external beam radiotherapy in European countries: An ESTRO-HERO analysis. Radiother Oncol. Jul. 2015;116(1):38-44.

Brenner et al. Computed Tomography—An Increasing Source of Radiation Exposure. N Engl J Med 2007; 357:2277-2284.

Brenner, D.J. Slowing the increase in the population dose resulting from CT scans. Radiat Res. Dec. 2010;174(6):809-15.

Delaney, G. et al. The role of radiotherapy in cancer treatment. Cancer. Sep. 15, 2005;104(6):1129-37.

Eslick E.M. et al. The Nano-X Linear Accelerator: A Compact and Economical Cancer Radiotherapy System Incorporating Patient Rotation. Technol Cancer Res Treat. Oct. 2015;14(5):565-72.

International Search Report and Written Opinion for PCT/US2022/017864, mailed Jul. 19, 2022, 22 pages.

Jinzaki, M. et al. Development of Upright Computed Tomography With Area Detector for Whole-Body Scans: Phantom Study, Efficacy on Workflow, Effect of Gravity on Human Body, and Potential Clinical Impact. Invest Radiol. Feb. 2020;55(2):73-83.

Jones et al. Radiation dose from medical imaging: a primer for emergency physicians. West J Emerg Med. May 2012;13(2):202-10.

Schreuder, N. et al. Fixed beamlines can replace gantries for particle therapy. Med Phys. Apr. 2022;49(4):2097-2100.

Siddiqui, et al. Radiation exposure among medical professionals working in the Intensive Care Unit. Indian J Crit Care Med. Sep. 2014; 18(9):591-595.

Taddei et al. Reducing stray radiation dose to patients receiving passively scattered proton radiotherapy for prostate cancer. Phys Med Biol. Apr. 21, 2008; 53(8):2131-2147.

Thariat et al. Past, present, and future of radiotherapy for the benefit of patients. Nat Rev Clin Oncol. Jan. 2013; 10(1):52-60.

Wall et al. Revised radiation doses for typical X-ray examinations. Report on a recent review of doses to patients from medical X-ray examinations in the UK by NRPB. National Radiological Protection Board. Br J Radiol. May 1997;70(833):437-9.

Yamada, Y. et al. Differences in Lung and Lobe Volumes between Supine and Standing Positions Scanned with Conventional and Newly Developed 320-Detector-Row Upright CT: Intra-Individual Comparison. Respiration. 2020;99(7):598-605.

* cited by examiner

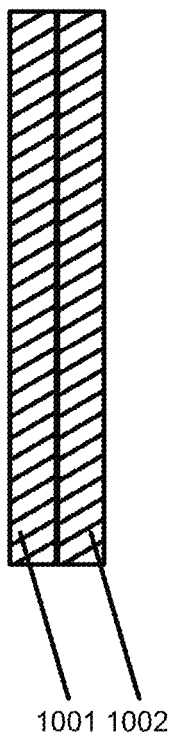
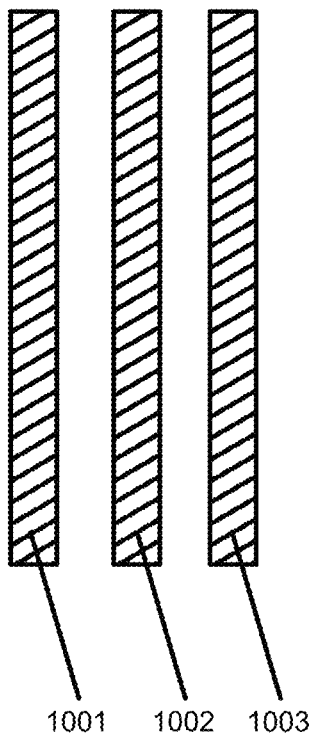
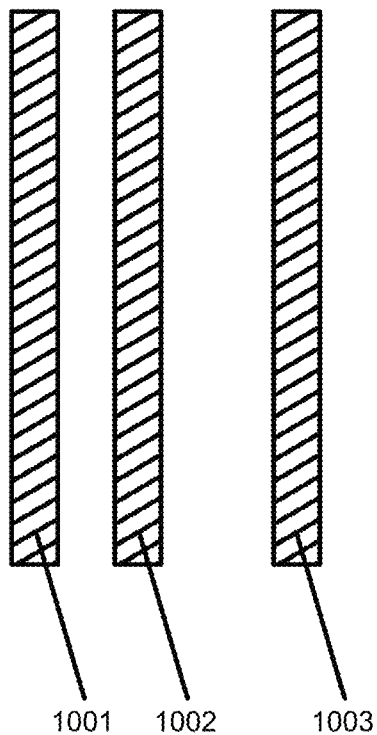
FIG. 10A  FIG. 10B  FIG. 10C
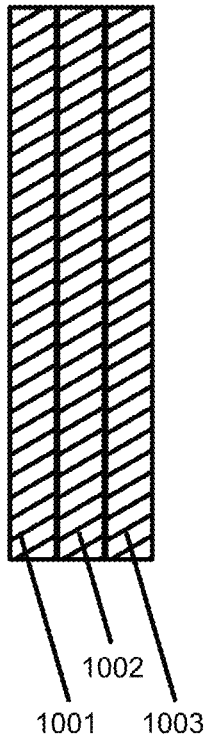
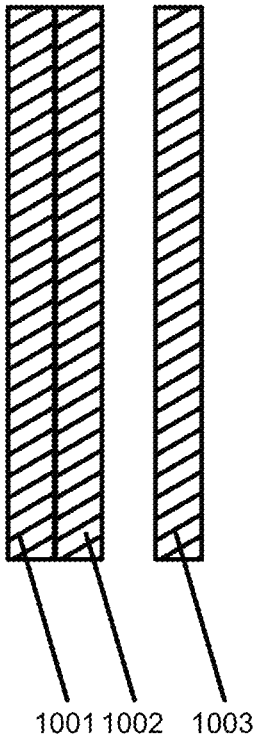
FIG. 10D  FIG. 10E

RADIATION PROTECTION

This application claims priority to U.S. provisional patent application Ser. No. 63/154,241, filed Feb. 26, 2021, which is incorporated herein by reference in its entirety.

FIELD

Provided herein is technology relating to controlling radiation and protecting biological organisms from exposure to radiation and particularly, but not exclusively, to apparatuses, methods, and systems for minimizing and/or eliminating exposure of humans to stray radiation used for medical imaging and therapy.

BACKGROUND

Medical imaging and medical therapies using radiation have contributed greatly to diagnosis and treatment of disease. While radiation-based technologies have benefited the diagnosis and treatment of patients for many diseases, these technologies also produce stray radiation that contributes to exposing patients and non-patients unnecessarily to radiation. Accordingly, technologies are needed to reduce exposure of humans to stray radiation produced by radiological imaging or radiotherapy treatment systems.

SUMMARY

Accordingly, provided herein is technology relating to controlling radiation and protecting biological organisms from exposure to radiation and particularly, but not exclusively, to apparatuses, methods, and systems for minimizing and/or eliminating exposure of humans to stray radiation used for medical imaging or therapy. In particular, the technology relates to minimizing and/or eliminating exposure of non-patients to stray radiation from imaging or treatment of a patient and/or to minimizing exposure of patients to stray radiation that results from leakage and/or backscatter.

The use of radiation to diagnose and treat patients produces stray radiation that can expose non-patients to radiation and expose a patient to non-useful and unnecessary exposure to radiation. Stray radiation includes leakage radiation, residual radiation, and scattered radiation from irradiated objects. These sources of stray radiation may expose non-patients to radiation when the non-patients are present in the room where a patient is being diagnosed (e.g., imaged) and/or treated using radiation. See, e.g., Siddiqui (2014) "Radiation exposure among medical professionals working in the Intensive Care Unit" Indian J Crit Care Med 18: 591, incorporated herein by reference. Non-patients outside the room where a patient is being diagnosed (e.g., imaged) and/or treated using radiation may also be exposed to stray radiation scattered from the treatment room into the space outside the treatment room or stray radiation that escapes from the treatment room into the space outside the treatment room due to insufficient shielding. Thus, some types of non-patients include the medical staff, doctors, and technicians present in the room to perform the diagnosis (e.g., imaging) or treatment of the patient and other medical and non-medical persons present in a hospital, clinic, or other treatment facility who are not involved with the diagnosis and/or treatment of the patient. Patients are exposed to unnecessary stray radiation due to leakage from the source and/or from backscatter of the imaging and/or treatment beam. See, e.g., Taddei (2008) "Reducing stray radiation dose to patients receiving passively scattered proton radiotherapy for prostate cancer" Phys Med Biol 53: 2131, incorporated herein by reference. Accordingly, the increased use of radiation for diagnosis (e.g., imaging) and treatment of patients causes an increased risk of radiation exposure both to patients and non-patients.

Both radiological imaging (e.g., x-ray imaging, computed tomography) and radiotherapy (e.g., external beam radiotherapy (e.g., x-ray therapy, electron therapy)) are in widespread and increasing use and present dangers of stray radiation to patients and non-patients. See, e.g., Brenner and Hall (2007) "Computed Tomography—An Increasing Source of Radiation Exposure" New England Journal of Medicine 357: 2277; and "Healthcare resource statistics— technical resources and medical terminology", *Statistics Explained*, Eurostat (European Union) publication dated Sep. 24, 2020, each of which is incorporated herein by reference. For instance, one study estimated in 2010 that more than 70 million CT scans are performed every year in the United States. See, e.g., Brenner (2010) "Slowing the increase in the population dose resulting from CT scans" Radiat Res 174: 809, incorporated herein by reference. With respect to radiotherapy, several estimates suggest that approximately half of all cancer cases should receive a form of radiotherapy during the course of treatment to provide optimal outcomes. (See, e.g., Delaney (2005) "The role of radiotherapy in cancer treatment" Cancer 104: 1129; and Borras (2015) "The optimal utilization proportion of external beam radiotherapy in European countries: An ESTRO-HERO analysis" Radiotherapy and Oncology 116: 38, each of which is incorporated herein by reference).

While use of radiotherapy is not as widespread as use of radiological imaging, the radiation doses used for radiotherapy are approximately 1000 times greater than the radiation doses used for imaging. For example, a typical dose from one CT scan is approximately 2-20 mSv and the typical dose from a cancer treatment is approximately 50,000 mSv to 100,000 mSv. (See, e.g., Wall and Hart (1997) "Revised radiation doses for typical x-ray examinations" The British Journal of Radiology 70: 437; Jones (2012) "Radiation Dose From Medical Imaging: A Primer for Emergency Physicians" Western Journal of Emergency Medicine: Integrating Emergency Care with Population Health, 13: 202; and Thariat et al. (2013) "Past, present, and future of radiotherapy for the benefit of patients" Nature Reviews Clinical Oncology 10: 52-60, each of which is incorporated herein by reference).

Conventional technologies for minimizing exposure to stray radiation generally use moderately large, permanent, or semi-permanent structures comprising large amounts of dense, heavy materials to minimize exposure to radiation outside the structure. These "bunker" structures are built with thick walls comprising large amounts of dense shielding material and/or are built with dimensions that keep non-patients outside the bunker walls at a safe distance from the source. For instance, shielding for photon sources typically uses concrete walls, ceilings, and floors that are 0.5 m to 5.0 m thick or more to surround a space that is the size of a typical large office. These solutions, however, increase materials and construction costs and do not sufficiently address exposure of patients and non-patients within the treatment room to leakage radiation and/or scattered radiation from the shielding walls. While increasing the size of the bunker dimensions and increasing the thickness of the bunker walls could decrease exposure of patients and non-patients within the treatment room to scattered radiation and decrease the exposure of non-patients outside the treatment room to stray radiation, increasing bunker dimensions and wall thicknesses further increases materials costs, construction costs, and the footprint of the bunker, which results in a structure that is impractically large and costly. As a result, conventional shielding solutions (e.g., shielding bunkers) are typically heavy, large, and immovable or difficult to move and thus are not appropriate for shielding a radiation source on a mobile platform.

Accordingly, provided herein is a radiation mitigation and/or control technology that reduces stray radiation (e.g., leakage, backscatter, and/or radiation that is scattered into the space outside a treatment room or that escapes into the space outside a treatment room) produced by a radiation source.

First, in some embodiments, the technology provides a design for a static (e.g., photon (e.g., x-ray)) source comprising shielding for the target. In some embodiments, the technology provides a static (e.g., photon (e.g., x-ray)) source comprising a narrow diameter waveguide ("snout") between the end of the linac electron source and the target. The narrow diameter waveguide has a diameter that is less than the diameter of the linac and allows shielding to be provided around the target to minimize leakage from the head. That is, the narrow diameter waveguide is a narrow cylinder enclosing both the target (e.g., near a distal end of the narrow diameter waveguide) and the final portion of the accelerated electron beam that contacts the target.

Second, in some embodiments, the technology described herein provides a radiation "trap" that minimizes and/or eliminates stray radiation produced by a static radiation source and scattering of the radiation produced by the static source. The radiation "trap" described herein thus reduces, minimizes, and/or eliminates the need for conventional shielding to be provided, e.g., by a bunker surrounding the radiation source and treatment room. In some embodiments, the technology provides a system to minimize stray radiation comprising both the narrow diameter waveguide and target shielding to minimize leakage and the radiation trap to minimize scatter and/or back-scatter.

In some embodiments, the radiation trap has a small size (e.g., has a small footprint). For example, an exemplary radiation trap provided herein for a photon (e.g., x-ray) source has dimensions (e.g., a length, width, and/or height) on the scale of several meters (e.g., a length, width, and/or height of approximately 1 to 5 m (e.g., approximately 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 m)).

In some embodiments, the combination of the narrow diameter wave guide allowing shielding around the target and the small size of the radiation trap reduces, minimizes, and/or eliminates the need for conventional bunker shielding and thus provides an improved technology that is appropriate for use with a mobile radiation source, e.g., for a mobile radiotherapy and/or mobile radiological imaging system. In particular, in some embodiments, the technology provides systems comprising a radiation source and a radiation trap as described herein provided on a mobile platform. In some embodiments, the technology provides systems comprising: 1) a radiation source comprising a narrow diameter waveguide between the linac and the target and shielding for the target as described herein; and 2) a radiation trap as described herein provided on a mobile platform. Systems (e.g., mobile systems) comprising the narrow diameter waveguide and target shielding and/or radiation trap technology comprise less material and have less mass and weight than conventional systems and are thus lighter than conventional technologies, less costly than conventional technologies, and more adaptable to mobile radiation sources than conventional systems.

In sum, the technology described herein provides protection from stray radiation to patients and non-patients inside and outside a treatment room using a narrow diameter waveguide and shielding around the target and/or a radiation trap technology that also allows a reduction in the thickness of conventional bunker shielding walls and/or a reduction in the dimensions of the treatment room containing the radiation source, patient, and/or medical personnel. Accordingly, in some embodiments, the technology relates to systems that combine improved target shielding and a small sized radiation trap to reduce the size and weight of the bunker shielding surrounding the source and treatment room to provide, e.g., mobile radiotherapy systems and/or mobile radiological imaging systems comprising a radiation source (e.g., comprising a narrow diameter waveguide and target shielding) and a radiation trap.

As described herein, the present technology both minimizes the dose outside the treatment room and minimizes exposure of non-patients and patients to stray (e.g., leakage, scattered, and/or backscattered) radiation inside the treatment room. For example, in some embodiments, the technology provided herein relates to a technology for radiation sources that minimizes and/or eliminates exposure of patients and/or others (e.g., non-patients) to stray radiation (e.g., due to leakage and/or backscatter). Accordingly, in some embodiments, the technology is provided for photon sources (e.g., electromagnetic radiation over a wide range of wavelengths (e.g., x-rays and gamma rays having a wavelength in the range of approximately 1 pm to approximately 1 nm)). In some embodiments, the technology provides protection from stray radiation (e.g., photon radiation) used for imaging. In some embodiments, the technology provides protection from stray radiation (e.g., photon radiation) used for therapy.

In some embodiments, the technology provides a static photon source comprising a narrow diameter waveguide between the linac electron source and the target and shielding around the target (e.g., to minimize and/or eliminate head leakage).

In an exemplary embodiment, the technology provided herein relates to a technology for a photon source (e.g., a static photon source (e.g., x-ray source) comprising a narrow diameter waveguide between the linac electron source and the target and comprising shielding around the target).

In some embodiments, the technology provided herein relates to a radiation "trap" for a photon source (e.g., a static photon source (e.g., x-ray source) comprising a narrow diameter waveguide between the linac electron source and the target and comprising shielding around the target) having an energy within the energy range typically used for treatment of a patient with a photon beam, e.g., approximately 4 to 25 MeV (e.g., approximately 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 MeV).

In some embodiments, the photon source (e.g., a static photon source comprising a narrow diameter waveguide between the linac electron source and the target and comprising shielding around the target) produces x-rays. In some embodiments, the technology relates to radiation trap technology for an x-ray source (e.g., a static x-ray source comprising a narrow diameter waveguide between the linac electron source and the target and comprising shielding around the target) having an energy within the energy range typically used for treatment of a patient with an x-ray beam (e.g., approximately 6 MV (e.g., approximately 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 MV)).

In an exemplary embodiment, the technology provided herein relates to a radiation trap technology for a photon (e.g., x-ray) source (e.g., a static photon (e.g., x-ray) source comprising a narrow diameter waveguide between the linac electron source and the target and comprising shielding around the target) used for imaging. In some embodiments, the technology provided herein relates to a radiation "trap" technology for a photon (e.g., x-ray) source (e.g., a static photon (e.g., x-ray) source comprising a narrow diameter waveguide between the linac electron source and the target and comprising shielding around the target) having an energy within the energy range typically used for imaging of a patient with a photon (e.g., x-ray) beam, e.g., approximately 40 to 150 kV (e.g., approximately 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 kV).

Furthermore, conventional therapy devices comprise an x-ray source that revolves around the subject and thus these conventional therapy devices require providing shielding 360 degrees around the subject. Accordingly, conventional shielding systems are large and require substantial amounts of shielding materials to provide 360-degree shielding. As a result, previous attempts to provide a sufficiently mobile radiotherapy system (e.g., in a bus, van, trailer, truck, or the like) comprising integrated shielding have failed due to the large sizes of the revolving radiotherapy source and the size and mass of the 360-degree shielding. Furthermore, some conventional mobile radiotherapy systems installed in a vehicle (e.g., bus, van, trailer, truck, or the like) require building an enclosing shielding structure (e.g., comprising several layers of stacked concrete blocks) to surround the system onsite and therefore are not completely mobile and do not comprise adequate shielding integrated into the system.

In contrast, embodiments of the present technology provide a radiation trap technology that finds use with a static radiation source, e.g., a static source used to image or treat a rotating patient. In some embodiments, the static photon (e.g., x-ray) source comprises a narrow diameter waveguide between the linac electron source and the target and comprising shielding around the target to minimize head leakage. The radiation trap technology provided herein is smaller (e.g., has a smaller volume and/or has one, two, or three smaller dimensions) and comprises less material (e.g., has a smaller mass) than conventional shields (e.g., 360-degree shields and/or shields that are essentially and/or substantially 360-degree shields) because a static source exposes a smaller volume of space to radiation (e.g., stray radiation (e.g., leakage and/or scatter)) than sources used in conventional technologies in which the source rotates around the patient. Furthermore, in some embodiments, the source comprises a narrow diameter waveguide between the linac electron source and the target, which allows shielding to be provided around the target to minimize leakage from the source, further reducing the amount of materials needed to minimize the stray radiation due to leakage and scatter.

Thus, in some embodiments, the technology provides a radiation shield that controls stray radiation in a volume on the other side of the patient from the beam (e.g., where the beam travels after passing through the patient and having, optionally, beam broadening and/or scatter). See, e.g., FIG. 1. In some embodiments, the radiation shield technology covers an arc centered on the patient that is less than 360 degrees, less than 180 degrees, less than 90 degrees, less than 45 degrees, and/or less than 30 degrees. Thus, in some embodiments, the technology provides a system comprising a static radiation source, a patient positioning system configured to rotate a patient, and an embodiment of the technology provided herein.

Furthermore, due the smaller size of the radiation trap technology provided herein relative to conventional shielding systems, in some embodiments, the technology described herein finds use on a smaller footprint than conventional shielding systems. For example, in some embodiments, the radiation trap technology described herein finds use in an office or on a mobile platform, e.g., a vehicle such as a bus, van, trailer, truck, or the like. In some embodiments, the technology described herein finds use as a component of an imaging and/or treatment system that is smaller than conventional imaging and/or treatment systems. In some embodiments, the technology described herein finds use as a component of an imaging and/or treatment system that is provided on a mobile platform, e.g., a vehicle such as a bus, van, trailer, truck, or the like. For example, in some embodiments, the technology provides a patient treatment system (e.g., comprising a static source comprising a narrow diameter waveguide between the linac electron source and the target and comprising shielding around the target and the radiation trap technology provided herein) that is provided on a mobile platform, e.g., a vehicle such as a bus, van, trailer, truck, or the like. In some embodiments, the technology provides a patient imaging system (e.g., comprising a static source comprising a narrow diameter waveguide between the linac electron source and the target and comprising shielding around the target and the radiation trap technology provided herein) that is provided on a mobile platform, e.g., a vehicle such as a bus, van, trailer, truck, or the like.

In addition, the present technology provides a more robust technology for minimizing and/or eliminating stray radiation than conventional technologies. For example, in some embodiments, the present technology provides an integrated patient imaging and/or treatment system comprising a static radiation source (e.g., a static source comprising a narrow diameter waveguide between the linac electron source and the target) and a radiation trap technology as described herein. Thus, the entire system can be checked for proper and safe function with respect to minimizing stray radiation and remedying insufficient shielding prior to installation. In contrast, conventional systems are subject to more failure modes than the present technology because conventional technologies first design a radiotherapy system and subsequently design a bunker to enclose the radiotherapy system, which is a complex engineering and construction undertaking that often has problems even for the most experienced people. A typical conventional workflow is, e.g., providing an imaging and/or therapy system, designing a bunker, constructing the bunker, installing the imaging and/or therapy system within the bunker, measuring the shielding provided by the bunker and/or measuring radiation scatter and/or escape from the bunker, and modifying the bunker to minimize scatter and/or escape of radiation from the bunker.

As described herein, the present technology provides a radiation trap technology that "catches" and/or "traps" the primary beam, e.g., by dissipating its energy to safe or less dangerous forms. In some embodiments, the radiation trap technology comprises a geometric arrangement configured to trap, e.g., absorb, scatter, and/or otherwise dissipate, radiation. In some embodiments, the radiation trap technology directs scattered radiation toward shielding and away from the patient. Furthermore, in some embodiments, the radiation trap technology comprises a shielding window that transmits high-energy radiation (e.g., from the primary beam) and absorbs and/or scatters lower-energy radiation. In some embodiments, the shielding window thus acts as a "radiation diode" that allows passage of high-energy radiation in one direction and stops passage of low-energy radiation returning from the other direction, e.g., due to back-scatter.

Thus, provided herein is technology related to a radiation trap. In some embodiments, the radiation trap comprises a chamber; a first barrier comprising a window that transmits high-energy radiation and absorbs and/or scatters low-energy radiation; and a second barrier. In some embodiments, the second barrier and the first barrier are parallel or substantially parallel and are positioned on opposing sides of the chamber, and, e.g., the first barrier is closer to a radiation source than the second barrier. In some embodiments, the radiation trap further comprises a lateral wall. In some embodiments the chamber comprises materials that absorb and/or scatter radiation within the chamber. In some embodiments, the chamber comprises materials having a Z that is less than the Z of the second and/or first barrier. In some embodiments, the second barrier and/or the first barrier comprise a high-density material. In some embodiments, the second barrier and/or the first barrier comprise lead. In some embodiments, the window comprises copper or aluminum. In some embodiments, a lateral wall comprises a high-density material. In some embodiments, the lateral wall comprises lead. In some embodiments, the first barrier is approximately 30 cm thick or approximately 20 cm thick (e.g., 15-40 cm thick (e.g., 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0 cm thick)). In some embodiments, the second barrier is approximately 36 cm thick (e.g., 15 to 40 cm thick (e.g., 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0 cm thick)). In some embodiments, the second barrier is approximately 60 cm (e.g., 50-70 (e.g., 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, or 70.0 cm)) from the first barrier. In some embodiments, the window is approximately 1-50 mm thick (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 mm thick).

In some embodiments, the chamber comprises materials arranged in a number of stratified layers arranged substantially parallel to the window and/or the second barrier. In some embodiments, the stratified layers are arranged to have an increasing Z as a function of distance from the window to the second barrier.

In some embodiments, the technology provides systems. For example, in some embodiments, a system comprising a radiation trap comprising a chamber; a first barrier comprising a window that transmits high-energy radiation and absorbs and/or scatters low-energy radiation; and a second barrier; and a static photon source. In some embodiments, systems further comprise a patient positioning system. In some embodiments, systems further comprise a mobile platform, e.g., in some embodiments, the system is provided on a mobile platform. In some embodiments, the mobile platform is a bus, van, trailer, or truck. In some embodiments, the static photon source comprises a narrow diameter waveguide between a linear accelerator (linac) of the static photon source and a target of the static photon source. In some embodiments, the static photon source comprises shielding around the target. In some embodiments, the patient positioning system is configured to rotate a patient. In some embodiments, the static photon source produces a beam of 4 to 25 MeV (e.g., approximately 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 MeV) or 40 to 150 kV (e.g., approximately 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 kV). In some embodiments, the system is a mobile bunker-free system. In some embodiments, the system further comprises a treatment room comprising the static photon source.

In some embodiments, the second barrier and the first barrier of the system are parallel or substantially parallel and are positioned on opposing sides of the chamber of the system and, in some embodiments, the first barrier is closer to a radiation source than the second barrier. In some embodiments, the radiation trap of the system further comprises a lateral wall. In some embodiments, the chamber of the system comprises materials that absorb and/or scatter radiation within the chamber. In some embodiments, the chamber comprises materials having a Z that is less than the Z of the second and/or first barrier. In some embodiments, the second barrier and/or the first barrier of the system comprise a high-density material. In some embodiments, the second barrier and/or the first barrier comprise lead. In some embodiments, the window of the system (e.g., of the chamber of the system) comprises copper or aluminum. In some embodiments, the lateral wall comprises a high-density material. In some embodiments, the lateral wall comprises lead. In some embodiments, the first barrier is approximately 30 cm thick or approximately 20 cm thick (e.g., 15-40 cm thick (e.g., 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0 cm thick)). In some embodiments, the second barrier is approximately 36 cm thick (e.g., 15 to 40 cm thick (e.g., 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0 cm thick)). In some embodiments, the second barrier is approximately 60 cm (e.g., 50-70 (e.g., 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, or 70.0 cm)) from the first barrier. In some embodiments, the window is approximately 1-50 mm thick (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 mm thick). In some embodiments, the chamber of the system comprises materials arranged in a number of stratified layers arranged substantially parallel to the window and/or the second barrier. In some embodiments, the stratified layers are arranged to have an increasing Z as a function of distance from the window to the second barrier. In some embodiments, the system is a therapy system or an imaging system. In some embodiments, the system further comprises a radiation beam (e.g., produced by the static source). In some embodiments, the system further comprises a photon beam (e.g., produced by the static source).

In some embodiments, the technology provides a method for treating a patient with radiation. For example, in some embodiments, methods comprise providing a radiation trap comprising a chamber; a first barrier comprising a window that transmits high-energy radiation and absorbs and/or scatters low-energy radiation; and a second barrier; and exposing a patient to radiation. In some embodiments, methods comprise rotating the patient. In some embodiments, methods comprise rotating the patient while exposing the patient to radiation. In some embodiments, methods comprise providing a patient positioning system. In some embodiments, methods comprise providing a narrow diameter waveguide between a linear accelerator (linac) of the static photon source and a target of the static photon source. In some embodiments, methods comprise providing shielding around the target of the static photon source. In some embodiments, the chamber comprises materials that absorb and/or scatter radiation within the chamber. In some embodiments, the chamber comprises materials having a Z that is less than the Z of the second and/or first barrier. In some embodiments, the window comprises copper or aluminum. In some embodiments, the chamber comprises materials arranged in a number of stratified layers arranged substantially parallel to the window and/or the second barrier. In some embodiments, the stratified layers are arranged to have an increasing Z as a function of distance from the window to the second barrier.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

In FIG. 1, the source 110 emits a radiation beam 120A/120B at a subject 130. The shielding trap comprises a first barrier 150, a chamber 160, and a second barrier 170. The first barrier 150 comprises a window 140. The window 140 comprises a material that transmits all, substantially all, and/or a major portion of the high-energy radiation from the beam into the chamber 160 and that primarily absorbs and/or scatters all, substantially all, and/or a major portion low-energy radiation originating from scatter within the chamber 160.

FIG. 2 shows the source 210 and subject 230. The shielding trap comprises first barrier 250, a chamber 260, and second barrier 270. The first barrier 250 comprises a window 240. The window 240 comprises a material that allows radiation to pass into the trap but not out of the trap.

FIG. 3 shows the source 310 and the subject 330. The source 310 comprises a collimation system 311 that shapes the beam to a treatment site. The shielding trap comprises first barrier 350, a chamber 360, and second barrier 370. The first barrier 350 comprises a window 340. The window 340 comprises a material that allows radiation to pass into the trap but not out of the trap.

FIG. 4 shows the source 410 and the subject 430. The radiation beam 420A/420B comprises the beam 420A that is emitted by the source 410 and the stray radiation 420B after the beam 420A passes through the subject 430. The shielding trap comprises first barrier 450, a chamber 460, and second barrier 470. The first barrier 450 comprises a window 440. The window 440 comprises a material that allows radiation to pass into the trap but not out of the trap.

FIG. 5 shows the source 510 and the subject 530. The radiation beam 520A/520B comprises the beam 520A that is emitted by the source 510 and the stray radiation 520B after the beam 520A passes through the subject 530. The shielding trap comprises first barrier 550, a chamber 560, and second barrier 570. The first barrier 550 comprises a window 540. The window 540 comprises a material and thickness that maximizes transmission of radiation into the trap and minimizes transmission out of the trap.

FIG. 5 shows the source 610 and the subject 630. The radiation beam 620A/620B comprises the beam 620A that is emitted by the source 610 and the stray radiation 620B after the beam 620A passes through the subject 630. The shielding trap comprises first barrier 650, a chamber 660, and second barrier 670. The first barrier 650 comprises a window (not shown).

FIG. 9 shows the position of the window 940 (in dotted lines) constructed within the first barrier 950. The chamber comprises a first lateral wall 910, a second lateral wall 920, and a second barrier 970. In some embodiments, the radiation shielding trap comprises a supplemental barrier 980, e.g., at a location where the beam energy is highly concentrated. The chamber comprises stratified layers 990A and 990B arranged to comprise materials having an increasing Z as a function of distance from the window to the second barrier (e.g., the Z of layer 990B>the Z of layer 990A). In some embodiments, the chamber comprises an intervening layer 990C comprising a material having a Z that is greater than or less than the Z of layer 990A and/or having a Z that is greater than or less than the Z of layer 990B.

FIG. 10A to 10E show non-limiting examples of arrangements for the stratified layers arranged to comprise a plurality of materials having an increasing Z as a function of distance from the window to the second barrier. In FIG. 10A to 10E, the window is to the left and the second barrier is to the right. FIG. 10A to 10E show two or three stratified layers. However, the technology is not limited to embodiments comprising two or three stratified layers of increasing Z as a function of distance from the window to the second barrier and thus includes embodiments comprising one, two, or three layers (e.g., 1, 2, 3, 4, 5, 6, 7, 8, 9, 10, 11, 12, 13, 14, 15, 16, 17, 18, 19, or 20 layers) and wherein any two and/or three layers can be arranged to be abutted, spaced, and/or with an intervening layer (e.g., as described herein and/or as shown in the examples shown in FIG. 10A to 10E). Further, while the thicknesses of the layers shown in FIG. 10A to 10E are drawn to appear the same, embodiments of the technology provide layers having any thickness that may be the same and/or different than the thickness(es) other layers in the stratified layers arranged in the chamber.

FIG. 10A shows two stratified layers 1001 and 1002 abutted against one another (e.g., 1001 contacts 1002) and where the Z of 1001 ($Z_{1001}$) is less than the Z of 1002 ($Z_{1002}$).

FIG. 10B shows three stratified layers 1001, 1002, and 1003 spaced equally (e.g., substantially and/or essentially equally) within the chamber and with intervening layers separating 1001 and 1002 and separating 1002 and 1003. In FIG. 10B, $Z_{1001}<Z_{1002}<Z_{1003}$.

FIG. 10C shows three stratified layers 1001, 1002, and 1003 spaced unequally within the chamber and with intervening layers separating 1001 and 1002 and separating 1002 and 1003. In FIG. 10C, $Z_{1001}<Z_{1002}<Z_{1003}$.

FIG. 10D shows three stratified layers 1001, 1002, and 1003 abutting against one another (e.g., 1001 contacts 1002 and 1002 contacts 1003). In FIG. 10D, $Z_{1001}<Z_{1002}<Z_{1003}$.

FIG. 10E shows three stratified layers 1001, 1002, and 1003; with 1001 and 1002 abutting against one another (e.g., 1001 contacts 1002); and with an intervening layer between 1002 and 1003. In FIG. 10D, $Z_{1001}<Z_{1002}<Z_{1003}$.

Figure 1:
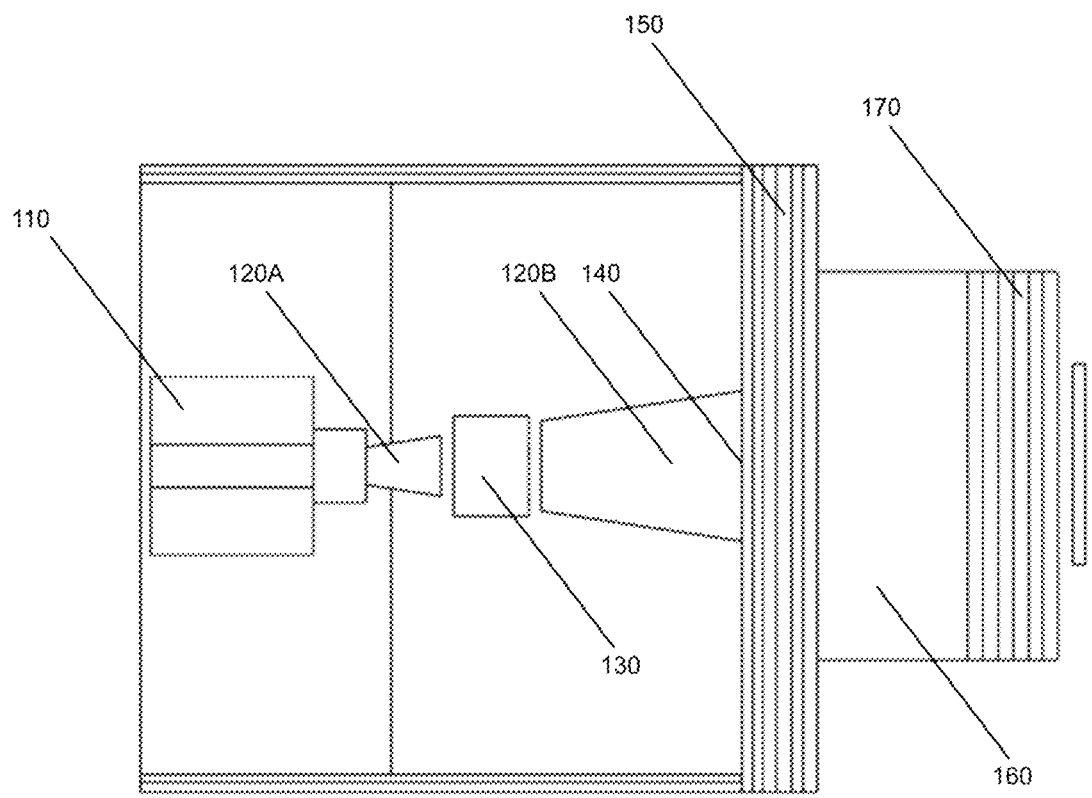
FIG. 1 is a schematic line drawing in plan view of an integrated radioimaging and/or radiotherapy system comprising a static radiation source and a shielding trap.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to controlling radiation and protecting biological organisms from exposure to radiation and particularly, but not exclusively, to apparatuses, methods, and systems for minimizing and/or eliminating exposure of humans to stray radiation used for medical imaging and therapy.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present" or "absent") is used in a relative sense to describe the amount or level of a particular entity (e.g., component, action, element). For example, when an entity is said to be "present", it means the level or amount of this entity is above a pre-determined threshold; conversely, when an entity is said to be "absent", it means the level or amount of this entity is below a pre-determined threshold. The pre-determined threshold may be the threshold for detectability associated with the particular test used to detect the entity or any other threshold. When an entity is "detected" it is "present"; when an entity is "not detected" it is "absent".

As used herein, an "increase" or a "decrease" refers to a detectable (e.g., measured) positive or negative change, respectively, in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling and directing methods.

As used herein, the term "leakage radiation" or "leakage" refers to radiation escaping from within the radiation source except for the radiation of the useful beam. Leakage may emanate from the source isotropically and may be scattered. In some embodiments, leakage radiation is controlled through the design of the tube housing and collimator filtering.

As used herein, the term "scattered radiation" refers to radiation that originates from interaction of the primary radiation with matter (e.g., the tissues of the patient and/or non-biological matter). In some embodiments, the interaction of the primary radiation with matter causes a change in direction (scattering) and/or a reduction in energy. Scattered radiation may originate from interactions of primary radiation with tissues of the patient and/or with other matter (e.g., before or after the beam, or a portion thereof, has passed through the tissues of the patient). Scattered radiation may result from elastic collisions or inelastic collisions of the radiation beam with matter. In an inelastic collision of the beam with matter, a portion of the energy from the radiation beam is absorbed by the matter with which the beam collides and the scattered radiation thus has a lower energy than the beam prior to collision.

As used herein, the term "stray radiation" refers to leakage radiation and/or scattered radiation.

As used herein, the term "primary radiation" refers to the useful beam emitted from the radiation source.

As used herein, the term "useful beam" refers to the part of radiation that passes through the exit opening of the source (e.g., aperture, diaphragm, or collimator) and is used for imaging and/or treatment.

As used herein, the term "beam" refers to a stream of radiation (e.g., electromagnetic wave and/or or particle radiation). In some embodiments, the beam is produced by a source and is restricted to a small-solid angle. In some embodiments, the beam is collimated. In some embodiments, the beam is generally unidirectional. In some embodiments, the beam is divergent.

As used herein, the term "half-value layer" (abbreviated "HVL") or "half-value thickness" (abbreviated "HVT") refers to the thickness of a material at which the intensity (e.g., energy) of radiation entering it is reduced by one half.

As used herein, the term "target", when used in reference to x-rays, refers to a piece of metal toward which electrons are accelerated (e.g., in a vacuum) (e.g., by an electric field) to produce x-rays. X-rays are emitted from the source as the electrons decelerate in the metal. The output comprises a continuous spectrum of x-rays that may comprise peaks at particular energies. In some embodiments, the continuous spectrum is due to bremsstrahlung and the peaks are characteristic x-rays associated with the atoms of the target.

Accordingly, the term "bremsstrahlung", when used in this context, refers to a spectrum of so-called "continuous x-rays".

As used herein, the term "bunker" or "radiation bunker" refers to a shield provided to protect an operator of a radiation source and/or non-patients outside of a treatment area from the harmful effects of radiation. Typically, the bunker fully or partially surrounds a room in which the radiation source and patient are present and/or is placed between the source and the operator and other non-patients. The radiation bunker is operable for shielding an operator and/or non-patients from the radiation source, the beam of radiation, and/or stray radiation.

As used herein, the term "patient" or "subject" refers to a mammalian animal that is identified and/or selected for imaging and/or treatment with radiation. Accordingly, in some embodiments, a patient or subject is contacted with a beam of radiation, e.g., a primary beam produced by a radiation source. In some embodiments, the patient or subject is a human. In some embodiments, the patient or subject is a veterinary or farm animal, a domestic animal or pet, or animal used for clinical research. In some embodiments, the subject or patient has cancer and/or the subject or patient has either been recognized as having or at risk of having cancer.

As used herein, the term "treatment volume" or "imaging volume" refers to the volume (e.g., tissue) of a patient that is selected for imaging and/or treatment with radiation. For example, in some embodiments, the "treatment volume" or "imaging volume" comprises a tumor in a cancer patient. As used herein, the term "healthy tissue" refers to the volume (e.g., tissue) of a patient that is not and/or does not comprise the treatment volume. In some embodiments, the imaging volume is larger than the treatment volume and comprises the treatment volume.

As used herein, the term "non-patient" refers to a mammalian animal that is not a patient or subject, e.g., an operator of a radiation source and/or other bystander or assistant who is not intended to be contacted by the beam of radiation.

As used herein, the term "radiation source" or "source" refers to an apparatus that produces radiation (e.g., ionizing radiation) in the form of photons (e.g., described as particles or waves). In some embodiments, a radiation source is a linear accelerator ("linac") that produces x-rays or electrons to treat a cancer patient by contacting a tumor with the x-ray or electron beam. In some embodiments, the source produces particles (e.g., photons, electrons, neutrons, hadrons, ions (e.g., protons, carbon ions, other heavy ions)). In some embodiments, the source produces electromagnetic waves (e.g., x-rays and gamma rays having a wavelength in the range of approximately 1 pm to approximately 1 nm). While it is understood that radiation can be described as having both wave-like and particle-like aspects, it is sometimes convenient to refer to radiation in terms of waves and sometimes convenient to refer to radiation in terms of particles. Accordingly, both descriptions are used throughout without limiting the technology and with an understanding that the laws of quantum mechanics provide that every particle or quantum entity may be described as either a particle or a wave.

As used herein, the term "static source" refers to a source that does not revolve around a patient during use of the source for imaging or therapy. In particular, a "static source" remains fixed with respect to an axis passing through the patient while the patient is being imaged or treated. While the patient may rotate around said axis to produce relative motion between the static source and rotating patient that is equivalent to the relative motion of a source revolving around a static patient, a static source does not move with reference to a third object, frame of reference (e.g., a treatment room in which a patient is positioned), or patient axis of rotation during imaging or treatment, while the patient may be rotated with respect to said third object, said frame of reference (e.g., said treatment room in which said patient is positioned), or patient axis of rotation through the patient during imaging or treatment. Thus, a static source may be installed on a mobile platform and thus the static source may move with respect to the Earth and fixtures on the Earth as the mobile platform moves to transport the static source. Thus, the term "static source" may refer to a mobile "static source" provided that the mobile "static source" does not revolve around an axis of rotation through the patient during imaging or treatment of the patient. Further, the static source may translate and/or revolve around the patient to position the static source prior to imaging or treatment of the patient or after imaging or treatment of the patient. Thus, the term "static source" may refer to a source that translates or revolves around the patient in non-imaging and non-treatment use, e.g., to position the source relative to the patient when the patient is not being imaged and/or treated. In some embodiments, the "static source" is a photon source and thus may be referred to as a "static photon source".

As used herein, the term "source comprising a narrow diameter waveguide between the linac electron source and the target and comprising shielding around the target" refers to the embodiment of the technology described herein in which a source comprises a narrow waveguide between the linac electron source and the target such that shielding can be placed around the target to minimize leakage from the source.

As used herein, the term "Z" refers to an atomic number (e.g., of an element and/or of a material comprising an element). As used herein, the "Z" of a material refers to the atomic number of the element or elements from which the material is made.

As used herein, the term "high-Z" refers to a chemical element that comprises a large number of protons in the nucleus, e.g., a chemical element having an atomic number that is 12 or more (e.g., 12 to 83). Exemplary "high-Z" chemical elements include, but are not limited to, copper (Cu), aluminum (Al), iron (Fe), titanium (Ti), tungsten (W), tantalum (Ta), lead (Pb), tin (Sn), antimony (Sb), and bismuth (Bi).

As used herein, the term "low-Z" refers to a chemical element that comprises a small number of protons in the nucleus, e.g., a chemical element having an atomic number that is from 1 to 11. Exemplary "low-Z" chemical elements include, but are not limited to, beryllium (Be), boron (B), carbon (C), hydrogen (H), oxygen (O), and nitrogen (N).

As used herein, the term "high-Z material" refers to a material comprising a "high-Z" chemical element, e.g., a material that is a pure, substantially pure, and/or effectively pure high-Z chemical element; and/or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a high-Z chemical element. In some embodiments, a high-Z material is a mixture, composite, alloy, ceramic, oxide, and/or a polymer comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a high-Z chemical element. In some embodiments, a high-Z material comprises embedded particles of a high-Z chemical element or a combination of high-Z chemical elements. In some embodiments, a high-Z material comprises a combination of two or more high-Z chemical elements, e.g., a material comprising two or more pure, substantially pure, and/or effectively pure high-Z chemical elements; or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a combination of two or more high-Z chemical elements (e.g., in a mixture, composite, alloy, ceramic, oxide, and/or a polymer).

As used herein, the term "low-Z material" refers to a material comprising a "low-Z" chemical element, e.g., a material that is a pure, substantially pure, and/or effectively pure low-Z chemical element; a molecule comprising low-Z chemical elements connected by chemical bonds; and/or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a low-Z chemical element or a molecule comprising low-Z chemical elements connected by chemical bonds. In some embodiments, a low-Z material is a mixture, composite, ceramic, oxide, and/or a polymer comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a low-Z chemical element or a molecule comprising low-Z chemical elements connected by chemical bonds. In some embodiments, a low-Z material comprises embedded particles of a low-Z chemical element or a molecule comprising low-Z chemical elements connected by chemical bonds; or comprises embedded particles comprising a combination of low-Z chemical elements or molecules comprising low-Z chemical elements connected by chemical bonds. In some embodiments, a low-Z material comprises a combination of two or more low-Z chemical elements or molecules comprising low-Z chemical elements connected by chemical bonds, e.g., a material comprising two or more pure, substantially pure, and/or effectively pure low-Z chemical elements or molecules comprising low-Z chemical elements connected by chemical bonds; or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a combination of two or more low-Z chemical elements or molecules comprising low-Z chemical elements connected by chemical bonds (e.g., in a mixture, composite, alloy, ceramic, oxide, and/or a polymer).

Description

The goal of radiotherapy is to deliver a maximum dose of radiation to a treatment volume in a patient (e.g., a tumor) while minimizing and/or eliminating exposure of healthy tissue in the patient and of other individuals, both inside and outside the treatment room, to stray radiation. In radiotherapy, providing an unobstructed path from the source (e.g., primary beam) to the treatment volume maximizes the radiation dose to the treatment volume of the patient. In addition to the beam contacting the treatment volume or imaging volume, radiological imaging and radiotherapy treatment systems can produce a number of types of stray radiation from the source (e.g., leakage from the source), from the beam (e.g., off-target portions of the beam, beam broadening), and from scattering of the beam (e.g., including back-scatter). Thus, radiological imaging and radiotherapy systems comprising radiation (e.g., photon (e.g., x-ray)) sources require radiation shielding, e.g., for safety of patients, operators, and bystanders; and as required by national and local regulations. Accordingly, shielding is provided to minimize and/or eliminate stray radiation from the beam (e.g., leakage from the source, off-path radiation) and stray scattered radiation that would contact healthy tissue or non-patients.

Accordingly, embodiments of the technology eliminate and/or minimize stray radiation within a treatment room to eliminate and/or minimize exposure of patient healthy tissue to radiation; embodiments of the technology eliminate and/or minimize stray radiation within a treatment room to eliminate and/or minimize exposure of non-patients in the treatment room to radiation; and embodiments of the technology eliminate and/or minimize stray radiation escaping from the treatment room to eliminate and/or minimize exposure of other non-patient individuals outside the treatment room to stray radiation. However, in contrast to previous radiation shielding technologies for radiation sources, the present technology comprises shielding for the target (e.g., to minimize leakage) and/or a radiation trap (e.g., to trap the primary beam and/or to minimize backscatter). The radiation trap is smaller and/or comprises less material than conventional shielding technologies. Further, embodiments of the technology provided herein relate to an integrated radiological imaging and/or radiotherapy system comprising a static radiation (e.g., x-ray) source (e.g., comprising a narrow diameter waveguide and target shielding) and a radiation trap that is smaller and comprises less material than conventional shields. In some embodiments, the technology provides an integrated radiation trap for a radiological imaging or radiotherapy system, e.g., a small and/or mobile radiological imaging or radiotherapy system (e.g., provided in a standard office or on a vehicle such as a bus, van, trailer, truck, or the like). In some embodiments, the technology relates to an integrated small and/or mobile radiological imaging and/or radiotherapy system, e.g., comprising a static radiation (e.g., photon (e.g., x-ray)) source (e.g., comprising a narrow diameter waveguide and target shielding) and a radiation trap that is smaller and comprises less material than conventional shielding technologies.

Radiation Shielding Trap

In some embodiments, the technology provided herein relates to a technology to minimize stray radiation by "catching" and/or "trapping" the primary radiation beam in a structure having a specific arrangement of materials to direct scattered radiation into shielding and away from the patient and other non-patient individuals. This specific arrangement of materials is referred to herein as a "trap" or a "shielding trap".

In some embodiments, e.g., as shown in FIG. 1, the technology provides an integrated radioimaging and/or radiotherapy system comprising a static radiation source and a shielding trap. In some embodiments, the source produces electromagnetic radiation (e.g., ionizing radiation). In some embodiments, the source is a linear accelerator (abbreviated "linac") that produces photons (e.g., x-rays). In some embodiments, the radiation source comprises and/or is surrounded by a shield comprising a high-Z material (e.g., in some embodiments, tungsten) or multiple high-Z materials. In some embodiments, the trap comprises a first barrier 150, a chamber 160, and a second barrier 170. In some embodiments, the first barrier and/or the second barrier comprise a high-Z material (e.g., in some embodiments, lead). In some embodiments, the second barrier and/or first barrier is/are thicker in an area where the beam is concentrated (e.g., in the center of the barrier(s)) and thinner away from the region where the beam is concentrated (e.g., away from the center of the barrier(s)). In some embodiments, the second barrier and/or first barrier comprises supplemental shielding in a region where the beam is concentrated. See, e.g., FIG. 9, supplemental barrier 980. Furthermore, in some embodiments, the trap comprises a first lateral wall, a second lateral wall, a floor, and/or a ceiling comprising a high-Z material (e.g., in some embodiments, lead).

Figure 2:
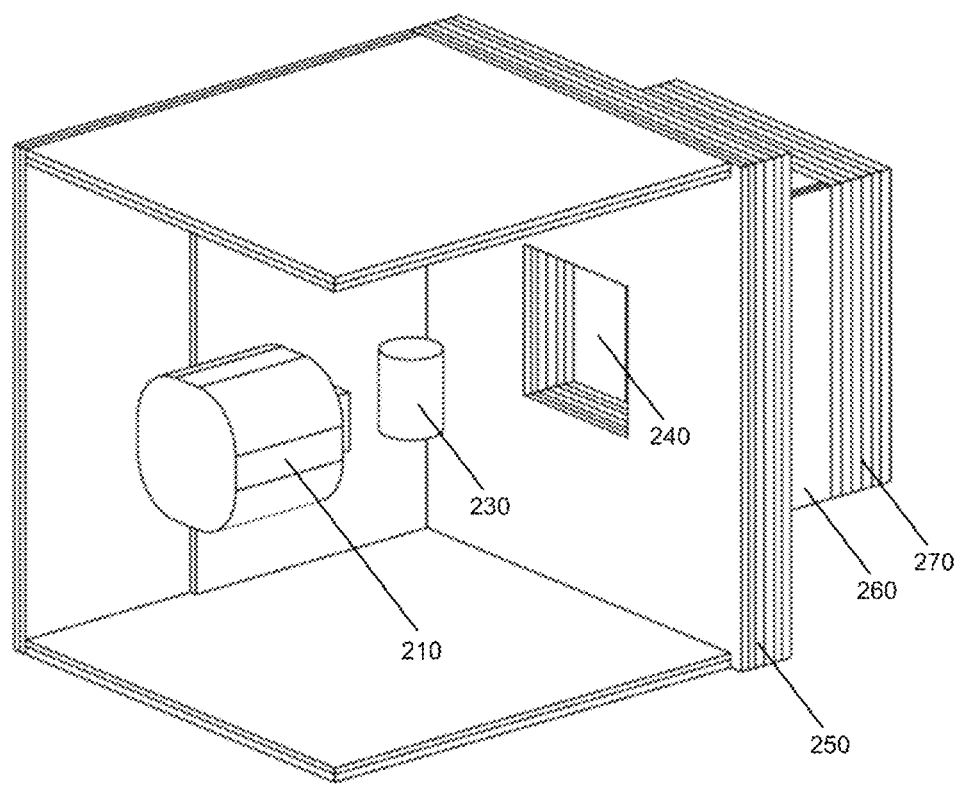
FIG. 2 is a schematic drawing in isometric projection of a radioimaging and/or radiotherapy system comprising a static radiation source and a shielding trap.
Figure 3:
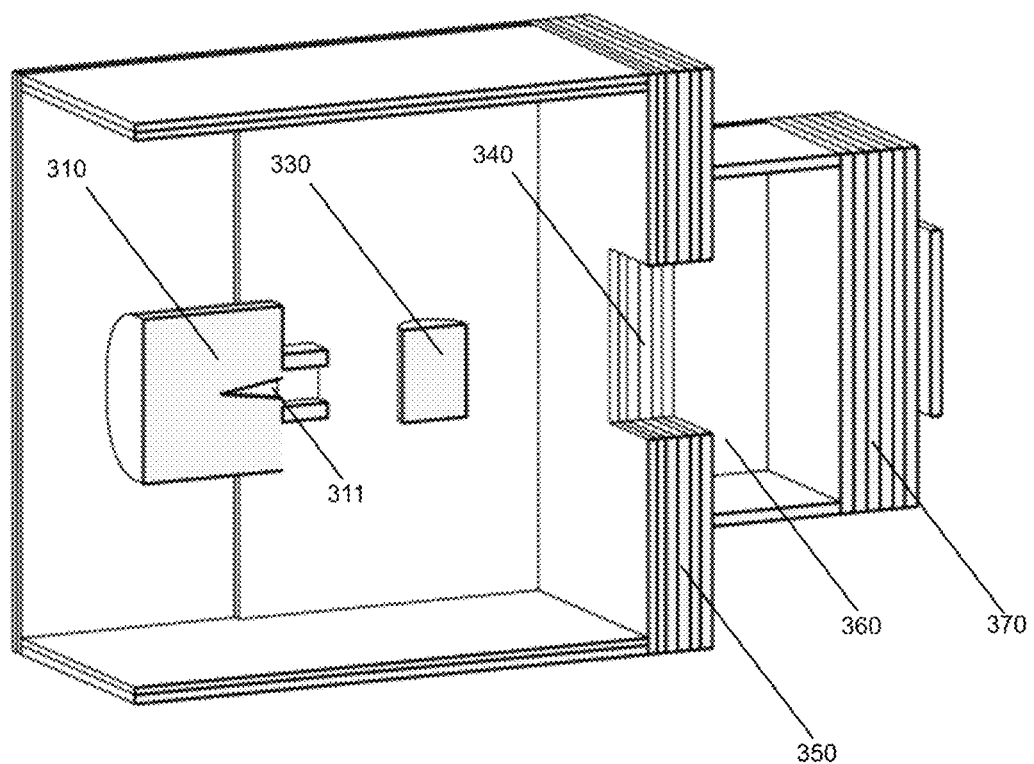
FIG. 3 is a schematic drawing in isometric projection showing a cutaway view of a radioimaging and/or radiotherapy system comprising a static radiation source and a shielding trap.
Figure 4:
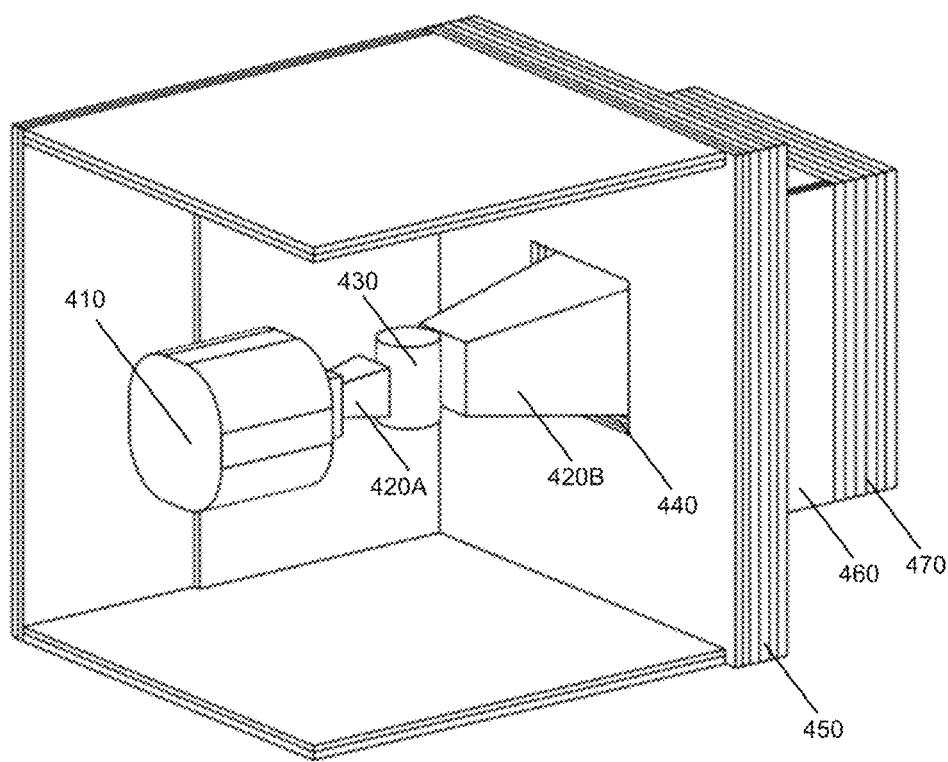
FIG. 4 is a schematic drawing in isometric projection of a radioimaging and/or radiotherapy system comprising a static radiation source and a shielding trap.
Figure 5:
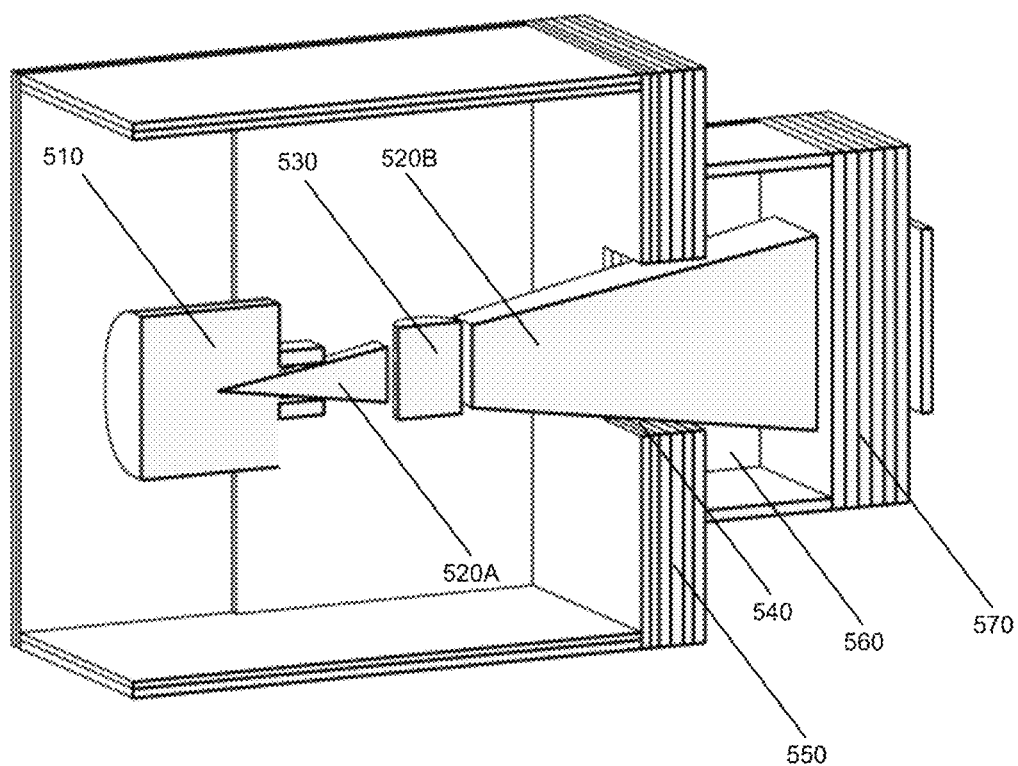
FIG. 5 is a schematic drawing in isometric projection showing a cutaway view of a radioimaging and/or radiotherapy system comprising a static radiation source and a shielding trap.
Figure 6:
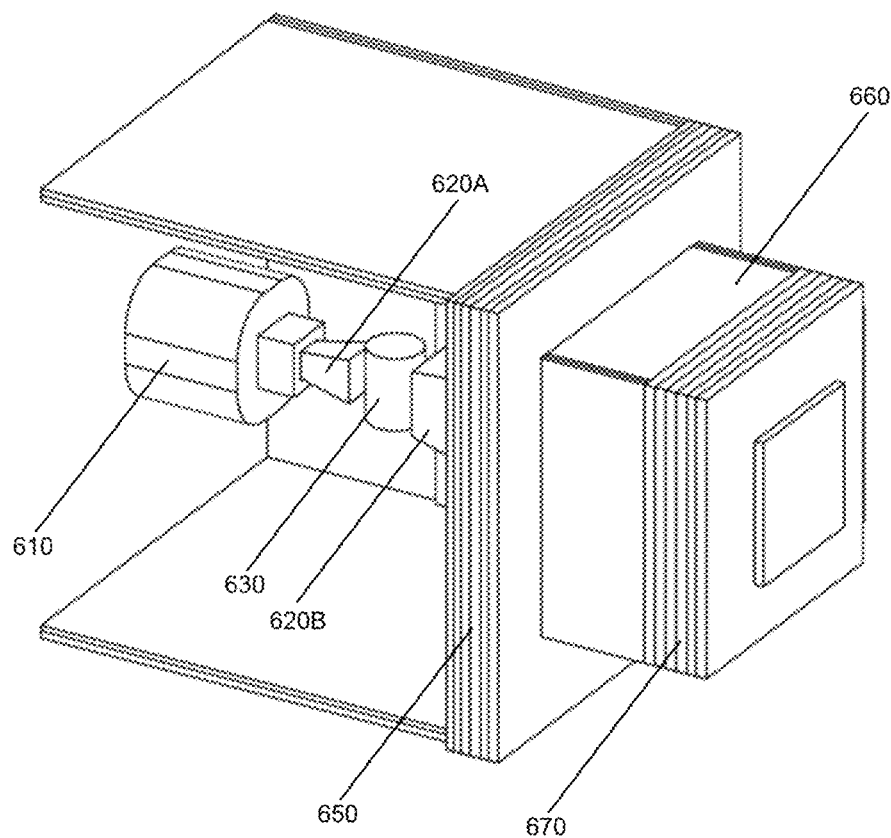
FIG. 6 is a schematic drawing in isometric projection of a radioimaging and/or radiotherapy system comprising a static radiation source and a shielding trap.

FIG. 2 is an oblique view of the source 210, subject 230, window 240, second barrier 270, chamber 260, and first barrier 250. FIG. 2 shows the space through which the beam travels from the source 210, through the subject 230, through the window 240, and into the radiation shielding trap (e.g., comprising the second barrier 270, chamber 260, and first barrier 250). The space through which the radiation beam travels may also be seen in FIG. 3, which shows the radiation source 310 and a collimation system 311 that shapes the beam for contacting a particular region of the subject 330. After the beam passes through the subject 330, it passes through the window 340 and into the chamber 360, where the beam radiation is scattered and absorbed by the second barrier 370 and the first barrier 350. FIG. 4 is an oblique view of the source 410, beam 420A, subject 430, stray radiation 420B, window 440, second barrier 470, chamber 460, and first barrier 450. FIG. 4 shows the path of the beam 420A from the source 410 and through the subject 430; and shows the subsequent path of the stray radiation 420B through the window 440 and into the radiation shielding trap (e.g., comprising the second barrier 470, chamber 460, and first barrier 450). The path of the radiation beam and stray radiation may be seen in FIG. 5. After the beam 520A is emitted by the source 510 and passes through the subject 530, the stray radiation 530B passes through the window 540 and into the chamber 560, where the beam radiation is scattered and absorbed by the second barrier 570 and the first barrier 550. An alternate view is shown in FIG. 6 showing the emission of the beam 620A from the source 610 through the subject 630 and travel of the stray radiation 620B through the window (not shown) into the radiation shielding trap comprising the second barrier 670, chamber 660, and first barrier 650.

As shown in FIG. 1, the path of the radiation beam 120A begins at the source 110. In some embodiments, a collimation system shapes the beam to the treatment site (e.g., the treatment volume) of a patient 130. See, e.g., FIG. 3, collimation system 311. Accordingly, in some embodiments, the collimation system helps to minimize and/or eliminate exposure of healthy patient tissue to radiation. The radiation beam 120A passes through the patient 130 and emerges as stray radiation 120B (e.g., having an energy $E_1$). The window comprises a material or multiple materials and/or is designed to have a thickness such that the stray radiation 120B (e.g., having an energy $E_1$) is maximally and/or completely transmitted through the window 140 and into the chamber 160 of the radiation shielding trap. In some embodiments, a portion of the stray radiation 120B (e.g., having an energy $E_1$) is absorbed by the window 140. In some embodiments, a portion of the stray radiation 120B (e.g., having an energy $E_1$) is scattered by the window 140, though the technology is designed to minimize and/or eliminate backscatter of stray radiation 120B by the window 140 into the treatment room and/or at the patient 130. Accordingly, the technology provides that essentially all and/or substantially all of the stray radiation 120B enters the chamber 160.

The radiation in the chamber is then absorbed and/or scattered within the chamber 160. In particular, radiation in the chamber is absorbed by the second barrier 170 furthest from the subject 130 and/or scattered by the materials within the chamber 160 of the trap at various angles, e.g., back toward the subject 130 and at other angles within the chamber 160. The materials and arrangement of materials in stratified layers of increasing Z within the chamber is described in more detail below. Radiation scattered back toward the subject 130 (e.g., having an energy $E_2<E_1$) is absorbed by the first barrier 150, absorbed by the window 140, and/or is scattered back into the chamber by the window 140. Radiation scattered at other angles within the chamber 160 of the trap is absorbed by the shielding of the lateral sides of the trap. Embodiments provide that small amounts of stray radiation 120B that do not pass through the window 140 are absorbed by the first barrier 150.

Shielding Trap Window

According to the shielding trap technology described herein, the trap comprises a window 140 (e.g., the first barrier comprises a window 140). See also FIG. 2, feature 240; FIG. 3, feature 340; FIG. 4, feature 440; and/or FIG. 5, feature 540). The window has a first side facing the radiation source and a second side facing the chamber of the shielding trap. The window is constructed (e.g., the window comprises a material and a thickness of said material) to maximize transmission of radiation from the beam into the chamber and to minimize and/or eliminate (substantially and/or essentially eliminate) scattering of radiation (e.g., high-energy radiation) impacting the first side of the window. In some embodiments, a portion of radiation impacting the window on the first side facing the radiation source is absorbed by the window.

Accordingly, high-energy radiation is maximally and/or totally transmitted through the window and into the chamber with minimal or no (e.g., substantially and/or essentially no) backscatter of the high-energy radiation directed toward the patient and/or non-patients inside or outside the treatment room. In some embodiments, the window comprises a material and a thickness of said material that maximizes transmission of radiation from the beam into the chamber and minimizes and/or eliminates (substantially and/or essentially eliminates) scattering of radiation (e.g., high-energy radiation) impacting the first side of the window. For example, in some embodiments, the window is made from copper or aluminum and is approximately 1-5 mm thick (e.g., approximately 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm thick). In some embodiments, the window absorbs radiation impacting it from either side.

Furthermore, the shape and dimensions of the window are larger than the projection of the beam onto the first barrier. Accordingly, the design maximizes the amount of radiation from the beam contacting the window and transmitting through the window and minimizes and/or eliminates (e.g., substantially and/or essentially eliminates) the radiation from the beam that does not contact the window for transmission into the chamber. In particular, the design maximizes the amount of radiation from the beam contacting the window and that is transmitted through the window and minimizes and/or eliminates (e.g., substantially and/or essentially eliminates) the radiation from the beam contacting the first barrier surrounding the window and/or other features, walls, persons, and/or structures in the treatment room. While the window is shown as having a square shape in FIGS. 2-5, embodiments provide that the shape of the window is not limited to any particular shape, provided that the shape and dimensions of the window are larger than the projection of the beam onto the first barrier. In some embodiments, the window is circular, polygonal (e.g., square), or oval.

The second side of the window is constructed (e.g., the window comprises a material and a thickness of said material) to maximize absorption of radiation scattered within the chamber and to minimize and/or eliminate (substantially and/or essentially eliminate) transmission of radiation from the chamber into the treatment room and toward the patient. The second side of the window absorbs and/or scatters the lower-energy scattered radiation contacting the second side of the window from within the chamber, thus minimizing and/or eliminating passage of the low-energy scattered radiation through the window into the treatment room and, consequently, minimizing and/or eliminating (substantially and/or essentially eliminating) transmission of the low-energy radiation through the window and into the treatment room.

Thus, the radiation trap technology provided herein is designed to maximize transmission of stray radiation from the primary beam into the chamber of the trap, where the radiation is scattered (e.g., in some embodiments, repeatedly scattered) by the materials within the chamber (see below) and reduced in energy and/or absorbed within the chamber; and to minimize transmission of radiation from the chamber into the treatment room and/or toward the patient.

Shielding Trap Chamber

The radiation shielding trap comprises a chamber, e.g., a chamber defined by a floor, a ceiling, a first lateral wall, a second lateral wall, the second barrier, and the first barrier comprising the window. Radiation transmitted through the window into the chamber is absorbed within the chamber and/or scattered within the chamber. In particular, the chamber comprises materials that absorb and/or scatter radiation within the chamber. In some embodiments, the materials within the chamber have a Z that is less than the Z of the second barrier, first barrier, lateral walls, ceiling, and floor of the chamber.

Figure 9:
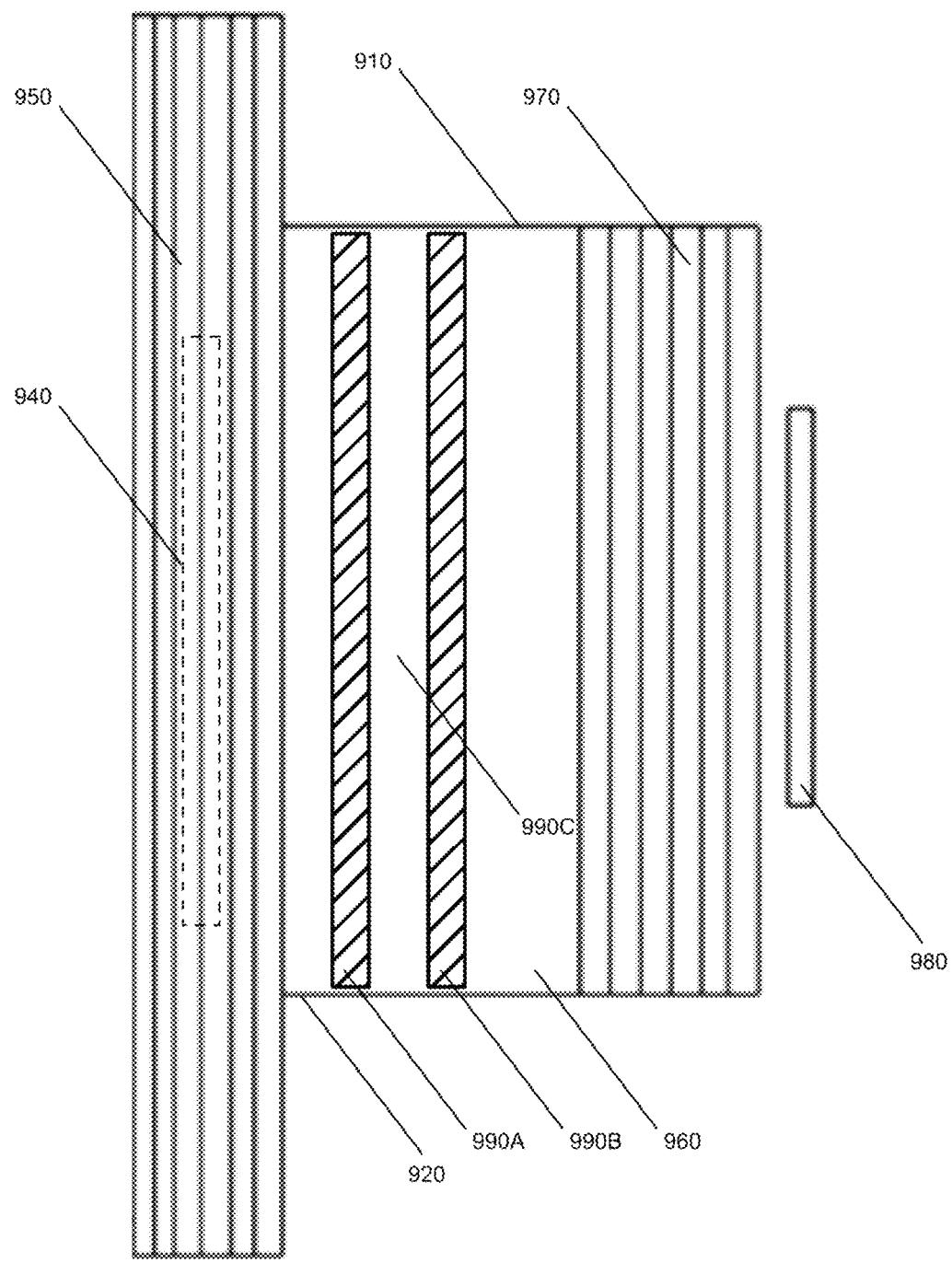
FIG. 9 is a schematic drawing in plan view of a chamber 960 of a radiation shielding trap.

For example, FIG. 9 shows a drawing of an exemplary embodiment of a chamber of the radiation trap technology provided herein. As shown in FIG. 9, in some embodiments, the technology provides a chamber 960 comprising a window 940 (in dotted lines) that is constructed within the first barrier 950. The chamber 960 further comprises a first lateral wall 910, a second lateral wall 920, and a second barrier 970. In some embodiments, the radiation shielding trap comprises a supplemental barrier 980. The supplemental barrier is configured to provide supplemental shielding in a region of the radiation trap (e.g., a region of the second barrier) where the beam radiation is most highly concentrated and/or where the beam energy is most concentrated.

Furthermore, as shown in FIG. 9, in some embodiments, the chamber 960 comprises materials arranged in a number of stratified layers (e.g., 990A, 990B) arranged parallel to (e.g., substantially and/or essentially parallel to) the window 940 and/or the second barrier 970. In some embodiments, the stratified layers (e.g., 990A, 990B) are arranged to comprise a plurality of materials having an increasing Z as a function of distance from the window 940 to the second barrier 970. That is, for a first layer 990A closer to the window 940 and made of a first material and a second layer 990B closer to the first barrier 970 and made of a second material, the Z of the first material is less than the Z of the second material; furthermore, in some embodiments, the Z of the first material and the Z of the second material are both less than the Z of the second barrier 970, first barrier 950, lateral walls 910 and 920, ceiling, and floor of the chamber. In some embodiments, the chamber comprises materials arranged in 2 to 20 layers (e.g., 2, 3, 4, 5, 6, 7, 8, 9, 10, 11, 12, 13, 14, 15, 16, 17, 18, 19, or 20 layers). The materials of the stratified layers may be made from a low-Z and/or a high-Z material. For example, in some embodiments, a stratified layer comprises a gas such as air.

In some embodiments, the stratified layers comprise an intervening layer (e.g., 990C) of a material that has a lower Z than a material closer to the window. For example, in some embodiments, the chamber comprises a layer L1 closer to the window, a layer L3 closer to the first barrier, and an intervening layer L2 between L1 and L3. Layer L1 comprises a material having a Z1 and layer L3 comprises a material Z3 where Z1<Z3, such that the chamber comprises stratified layers that are arranged to comprise a plurality of materials having an increasing Z as a function of distance from the window to the second barrier. However, intervening layer L2 may be made of a material that has a Z2 that is greater than Z1 or that is less than Z1 and/or L2 may be made of a material that has a Z2 that is greater than Z3 or that is less than Z3. For example, L1 and L3 may be separated by an air gap layer.

Embodiments of the chamber (e.g., a chamber 960 as shown in FIG. 9) comprise stratified layers provided in a number of different arrangements, e.g., as shown in FIG. 10A to FIG. 10E. For example, as shown in FIG. 10A, in some embodiments, the chamber comprises two stratified layers 1001 and 1002 abutted against one another (e.g., 1001 contacts 1002) and where the Z of 1001 ($Z_{1001}$) is less than the Z of 1002 ($Z_{1002}$). In some embodiments, e.g., as shown in FIG. 10B, the chamber comprises three stratified layers 1001, 1002, and 1003 spaced equally (e.g., substantially and/or essentially equally) within the chamber and with intervening layers separating 1001 and 1002 and separating 1002 and 1003. In FIG. 10B, $Z_{1001}<Z_{1002}<Z_{1003}$. In some embodiments, e.g., as shown in FIG. 10C, the chamber comprises three stratified layers 1001, 1002, and 1003 spaced unequally within the chamber and with intervening layers separating 1001 and 1002 and separating 1002 and 1003 and with $Z_{1001}<Z_{1002}<Z_{1003}$. In some embodiments, e.g., as shown in FIG. 10D, the chamber comprises three stratified layers 1001, 1002, and 1003 abutting against one another (e.g., 1001 contacts 1002 and 1002 contacts 1003) and with $Z_{1001}<Z_{1002}<Z_{1003}$. In some embodiments, e.g., as shown in FIG. 10E, the chamber comprises three stratified layers 1001, 1002, and 1003; with 1001 and 1002 abutting against one another (e.g., 1001 contacts 1002); with an intervening layer between 1002 and 1003; and with $Z_{1001}<Z_{1002}<Z_{1003}$. While FIG. 10A to 10E show examples of arrangements for the stratified layers provided within the chamber to provide a plurality of materials having an increasing Z as a function of distance from the window to the second barrier, the technology is not limited to the arrangements of two or three layers shown in FIG. 10A to 10E. The technology provides embodiments of the radiation trap comprising one, two, or three layers (e.g., 1, 2, 3, 4, 5, 6, 7, 8, 9, 10, 11, 12, 13, 14, 15, 16, 17, 18, 19, or 20 layers) and wherein any two and/or three layers can be arranged to be abutted against one another or spaced apart from one another (e.g., comprising an intervening layer). While the thicknesses of the layers shown in FIG. 10A to 10E are drawn to appear the same, embodiments of the technology provide layers having any thickness that may be the same and/or different than the thickness(es) other layers in the stratified layers arranged in the chamber.

Shielding Trap for Photon Source

In some embodiments, the technology provides a radiation trap for a photon source (e.g., a static photon source) and/or a system (e.g., a mobile system) comprising a photon source (e.g., a static photon source) and a radiation trap for the photon source, wherein the photon source (e.g., static photon source) and the radiation trap are provided on a mobile platform.

In some embodiments, the photon source is a static photon (e.g., x-ray) source comprising a narrow diameter waveguide between the end of the linac electron source and the target, e.g., as described further below. Thus, in some embodiments, the technology provides a radiation trap for a photon source (e.g., a static photon (e.g., an x-ray) source) and/or a system (e.g., a mobile system) comprising a photon source (e.g., a static photon (e.g., x-ray) source) and a radiation trap for the photon source (e.g., a static photon (e.g., an x-ray) source), wherein the photon source (e.g., static photon (e.g., x-ray) source) and the radiation trap are provided on a mobile platform.

Embodiments providing a radiation trap for a photon source may be constructed with particular dimensions and materials as appropriate for the energy of the photon source. For example, in some embodiments, the technology provides a radiation trap for a photon source having an energy within the energy range typically used for treatment of a patient with a photon beam, e.g., approximately 4 to 25 MeV (e.g., approximately 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 MeV). In some embodiments, the technology provides a radiation trap for x-ray source having an energy within the energy range typically used for treatment of a patient with an x-ray beam, e.g., approximately 6 MV (e.g., approximately 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 MV)). In some embodiments, the technology provides a radiation trap for a photon source (e.g., an x-ray source) having an energy within the energy range typically used for imaging a patient with a photon source (e.g., x-ray source), e.g., approximately 40 to 150 kV (e.g., approximately 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 kV).

Figure 7:
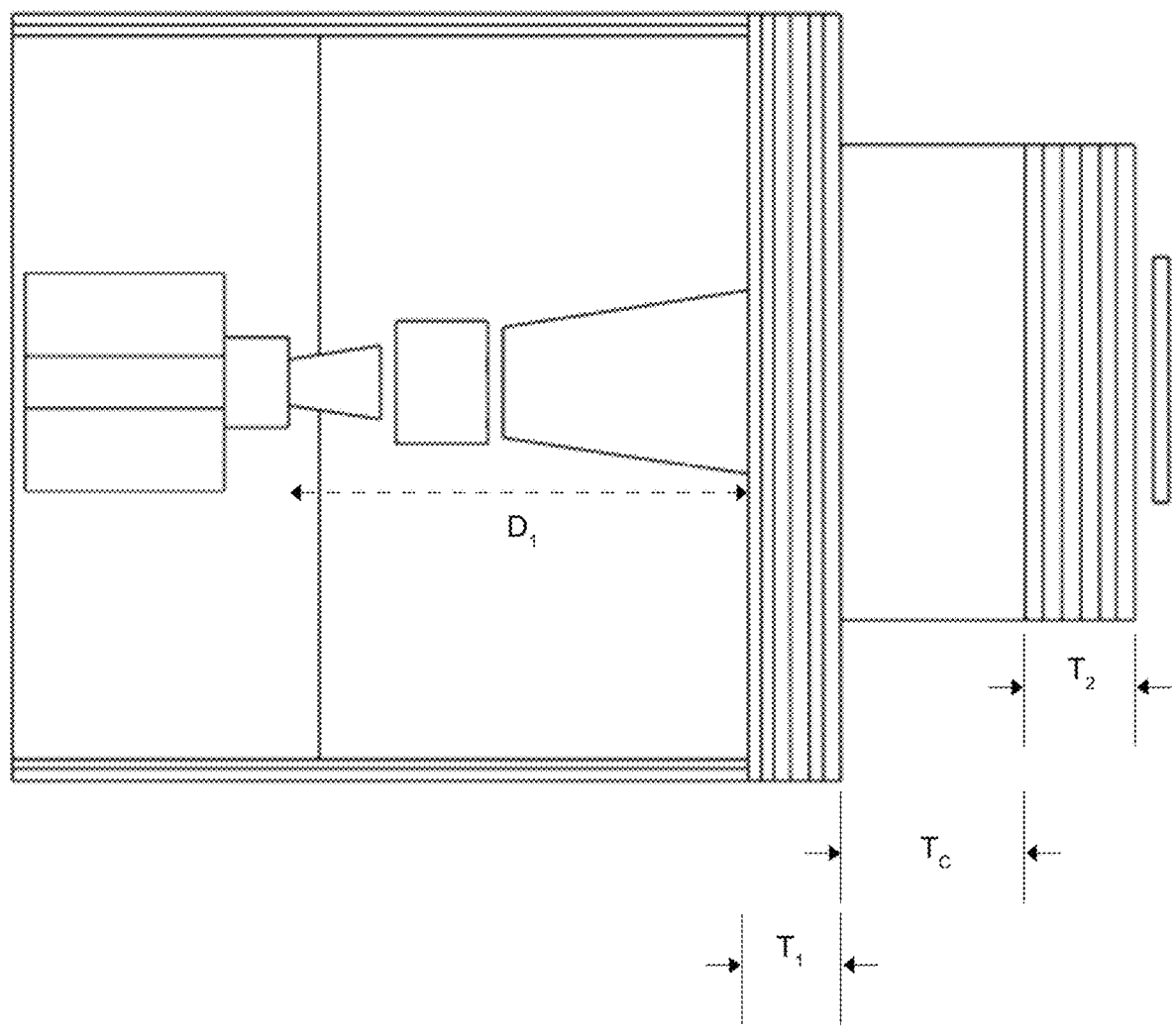
FIG. 7 is a schematic line drawing in plan view of an integrated radioimaging and/or radiotherapy system comprising a static radiation source and a shielding trap. The distance from the source to the first barrier ($D_1$), the thickness of the first barrier ($T_1$), the thickness of the second barrier ($T_2$), and the thickness of the chamber ($T_C$, distance from primary to second barrier) are indicated and particular dimensions are provided herein.

In some embodiments, the shielding trap finds use with a photon source (e.g., a photon source for therapy and/or imaging). For example, in some embodiments, the first barrier has a thickness ($T_1$) of approximately 30 cm (e.g., approximately 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0 cm thick). See, e.g., FIG. 7. In some embodiments, the first barrier has a thickness ($T_1$) of approximately 20 cm (e.g., 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0 cm thick). See, e.g., FIG. 7. In some embodiments, the second barrier has a thickness ($T_2$) of approximately 36 cm (e.g., approximately 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, or 45.0 cm thick). See, e.g., FIG. 7. In some embodiments, the distance across the chamber ($T_C$, e.g., from the first barrier to the second barrier) is approximately 60 cm (e.g., approximately 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, or 75.0 cm). See, e.g., FIG. 7.

In some embodiments, the distance from the source to the first barrier ($D_1$) is approximately 200 cm (e.g., 180.0, 180.5, 181.0, 181.5, 182.0, 182.5, 183.0, 183.5, 184.0, 184.5, 185.0, 185.5, 186.0, 186.5, 187.0, 187.5, 188.0, 188.5, 189.0, 189.5, 190.0, 190.5, 191.0, 191.5, 192.0, 192.5, 193.0, 193.5, 194.0, 194.5, 195.0, 195.5, 196.0, 196.5, 197.0, 197.5, 198.0, 198.5, 199.0, 199.5, 200.0, 200.5, 201.0, 201.5, 202.0, 202.5, 203.0, 203.5, 204.0, 204.5, 205.0, 205.5, 206.0, 206.5, 207.0, 207.5, 208.0, 208.5, 209.0, 209.5, 210.0, 210.5, 211.0, 211.5, 212.0, 212.5, 213.0, 213.5, 214.0, 214.5, 215.0, 215.5, 216.0, 216.5, 217.0, 217.5, 218.0, 218.5, 219.0, 219.5, or 220.0 cm). See, e.g., FIG. 7.

Figure 8:
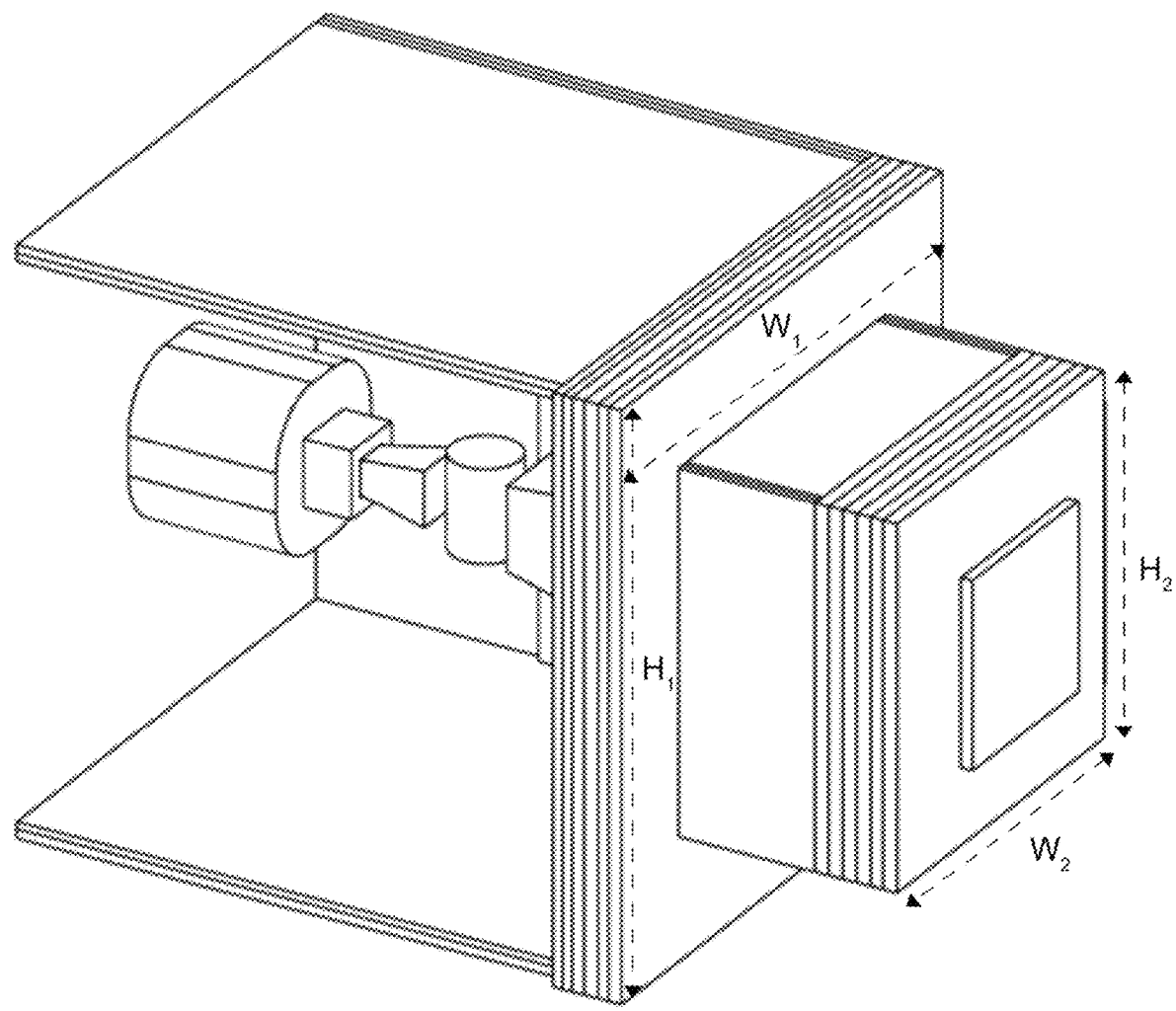
FIG. 8 is a schematic drawing in isometric projection of a radioimaging and/or radiotherapy system comprising a static radiation source and a shielding trap. The height ($H_2$) and width ($W_2$) of the second barrier and the height ($H_1$) and width ($W_1$) of the first barrier are indicated and particular dimensions are provided herein.

In some embodiments, the second barrier has a height ($H_2$) and a width ($W_2$). See, e.g., FIG. 8. In some embodiments, the height ($H_2$) and/or the width ($W_2$) of the second barrier is approximately 150 cm (e.g., 140.0, 140.5, 141.0, 141.5, 142.0, 142.5, 143.0, 143.5, 144.0, 144.5, 145.0, 145.5, 146.0, 146.5, 147.0, 147.5, 148.0, 148.5, 149.0, 149.5, 150.0, 150.5, 151.0, 151.5, 152.0, 152.5, 153.0, 153.5, 154.0, 154.5, 155.0, 155.5, 156.0, 156.5, 157.0, 157.5, 158.0, 158.5, 159.0, 159.5, or 160.0 cm). See, e.g., FIG. 8. In some embodiments, the second barrier comprises a surface that is rounded, curved, hyperbolic, parabolic, ellipsoid, etc. that when projected onto a plane normal or substantially normal to the path of the primary beam, the projection of the second barrier on the plane has a height and/or width that is approximately 150 cm (e.g., 140.0, 140.5, 141.0, 141.5, 142.0, 142.5, 143.0, 143.5, 144.0, 144.5, 145.0, 145.5, 146.0, 146.5, 147.0, 147.5, 148.0, 148.5, 149.0, 149.5, 150.0, 150.5, 151.0, 151.5, 152.0, 152.5, 153.0, 153.5, 154.0, 154.5, 155.0, 155.5, 156.0, 156.5, 157.0, 157.5, 158.0, 158.5, 159.0, 159.5, or 160.0 cm). In some embodiments, the first barrier has a height ($H_1$) and a width ($W_1$). See, e.g., FIG. 8. In some embodiments, the height ($H_1$) and/or the width ($W_1$) of the first barrier is approximately 240 cm (e.g., 220.0, 220.5, 221.0, 221.5, 222.0, 222.5, 223.0, 223.5, 224.0, 224.5, 225.0, 225.5, 226.0, 226.5, 227.0, 227.5, 228.0, 228.5, 229.0, 229.5, 230.0, 230.5, 231.0, 231.5, 232.0, 232.5, 233.0, 233.5, 234.0, 234.5, 235.0, 235.5, 236.0, 236.5, 237.0, 237.5, 238.0, 238.5, 239.0, 239.5, 240.0, 240.5, 241.0, 241.5, 242.0, 242.5, 243.0, 243.5, 244.0, 244.5, 245.0, 245.5, 246.0, 246.5, 247.0, 247.5, 248.0, 248.5, 249.0, 249.5, 250.0, 250.5, 251.0, 251.5, 252.0, 252.5, 253.0, 253.5, 254.0, 254.5, 255.0, 255.5, 256.0, 256.5, 257.0, 257.5, 258.0, 258.5, 259.0, 259.5, or 260.0 cm). See, e.g., FIG. 8.

In some embodiments, the chamber comprises one or more materials having a Z less than the Z of the second barrier and/or first barrier.

As described herein, embodiments of the technology provide a radiation shielding trap comprising a number of materials and material thicknesses to minimize and/or eliminate stray radiation from the beam. In particular, the radiation trap comprises a thick shielding material (e.g., the second barrier, first barrier, lateral walls, ceiling, and floor of the trap), a chamber, and a window comprising a material that maximally transmits radiation into the chamber and minimally transmits radiation out of the chamber. While a similar design would prohibitively complicate a conventional radiation shield and bunker because conventional shields and bunkers have a greater size to surround rotating sources with 360-degree protection, the technology described herein provides an improved technology for a static radiation source because the radiation trap described herein is smaller than conventional bunkers and thus can be made with a more robust design to concentrate shielding into the area where the beam is focused, thus both minimizing costs and maximizing safety.

Thus, the technology provided herein provides the advantage of minimizing and/or eliminating stray radiation and the scatter of radiation directed back to the patient (e.g., by scattering the radiation in an area away from the patient instead of towards it). In addition, in some embodiments, the technology provides a radiation trap and/or an integrated radiation source and radiation trap that has a small footprint and thus can be installed in an office or on a mobile platform (e.g., a bus, van, trailer, truck, or the like). The technology requires less material than conventional shields and associated bunkers. The technology requires a smaller room or space than conventional shields and bunkers. Thus, the technology uses less space and less materials than conventional technologies.

Radiation Source Comprising Narrow Diameter Waveguide and Target Shielding

In some embodiments, the technology provides a design for a static photon source comprising shielding for the target. In some embodiments, the technology provides a static photon source comprising a narrow diameter waveguide between the end of the linac electron source and the target. The narrow diameter wave guide has a diameter that is less than the diameter of the linac and allows shielding to be provided around the target to minimize leakage from the head. That is, the narrow diameter waveguide is a narrow cylinder enclosing the target (e.g., near a distal end of the narrow diameter waveguide) and the final portion of the accelerated electron beam that contacts the target.

Integrated Shielding Trap

In some embodiments, the technology provides an integrated radioimaging and/or radiotherapy system comprising a static radiation source and a shielding trap as described herein and as shown in FIGS. 1 to 10E. In some embodiments, the technology provides a treatment room comprising an integrated radioimaging and/or radiotherapy system comprising a static radiation source and a shielding trap as described herein and as shown in FIGS. 1 to 10E.

In some embodiments, the static radiation source of the integrated radioimaging and/or radiotherapy system is a photon source. In some embodiments, the static radiation source of the integrated radioimaging and/or radiotherapy system is an x-ray source. In some embodiments, the static radiation source (e.g., photon source (e.g., x-ray source)) comprises a narrow diameter wave guide between the linac electron source and the target and comprises shielding around the target, e.g., as described herein (e.g., to minimize head leakage).

In some embodiments, the integrated radioimaging and/or radiotherapy system comprising a static radiation source (e.g., photon source (e.g., x-ray source)) comprising a narrow diameter waveguide between the linac electron source and the target and comprising shielding around the target) and a shielding trap is mobile, e.g., provided on a vehicle such as a bus, van, trailer, truck, or the like. In some embodiments, the integrated radioimaging and/or radiotherapy system comprising a static radiation source (e.g., photon source (e.g., x-ray source)) comprising a narrow diameter waveguide between the linac electron source and the target and comprising shielding around the target) and a shielding trap is bunker-free (e.g., is not surrounded by an additional bunker to supplement the shielding trap described herein). Accordingly, in some embodiments, the technology provides a mobile integrated radioimaging and/or radiotherapy system comprising a static radiation source (e.g., photon source (e.g., x-ray source)) comprising a narrow diameter waveguide between the linac electron source and the target and comprising shielding around the target), a shielding trap, and a mobile platform (e.g., a vehicle (e.g., a bus, van, trailer, truck, or the like)). In some embodiments, the technology provides a mobile integrated radioimaging and/or radiotherapy system comprising treatment room, a static radiation source (e.g., photon source (e.g., x-ray source)) comprising a narrow diameter waveguide between the linac electron source and the target and comprising shielding around the target), a shielding trap, and a mobile platform (e.g., a vehicle (e.g., a bus, van, trailer, truck, or the like)). In some embodiments, the technology provides a mobile integrated radioimaging and/or radiotherapy system comprising treatment room, a static radiation source (e.g., photon source (e.g., x-ray source)) comprising a narrow diameter waveguide between the linac electron source and the target and comprising shielding around the target), a shielding trap, a patient positioning system (e.g., as described in Int'l Pat. App. Pub. No. WO 2019/056055 and U.S. Pat. App. Pub. No. 2020/0268327, each of which is incorporated herein by reference), and a mobile platform (e.g., a vehicle (e.g., a bus, van, trailer, truck, or the like)). In some embodiments, the technology provides an integrated radioimaging and/or radiotherapy system comprising a treatment room, a static radiation source (e.g., photon source (e.g., x-ray source)) comprising a narrow diameter waveguide between the linac electron source and the target and comprising shielding around the target), a shielding trap, and a patient positioning system (e.g., as described in Int'l Pat. App. Pub. No. WO 2019/056055 and U.S. Pat. App. Pub. No. 2020/0268327, each of which is incorporated herein by reference).

While, in some embodiments, the radiation trap is provided as part of an integrated system comprising a radiation source (e.g., photon source (e.g., x-ray source)) comprising a narrow diameter waveguide between the linac electron source and the target and comprising shielding around the target) and the radiation trap described herein, in some embodiments, the radiation trap is not integrated into a system comprising a radiation source and is provided as a stand-alone radiation trap, e.g., for use with a radiation source but not integrated into a system with the radiation source. Accordingly, in some embodiments, the technology provides a radiation trap without a source (e.g., a source-free shielding trap). In some embodiments, the technology provides a radiation trap (e.g., a source-free trap) comprising a second barrier 170, a chamber 160, and a first barrier 150 comprising a window 140. In some embodiments, the first barrier and/or the second barrier comprise a high-Z material. In some embodiments, the chamber comprises materials arranged in a number of stratified layers arranged parallel to (e.g., substantially and/or essentially parallel to) the window and/or the second barrier and arranged to comprise a plurality of materials having an increasing Z as a function of distance from the window to the second barrier (as described herein).

Methods

In some embodiments, the technology relates to imaging methods and/or treatment methods. In some embodiments, the technology relates to methods of minimizing and/or eliminating stray radiation produced by a radiation source used for imaging or treatment. In some embodiments, methods comprise providing an integrated radioimaging and/or radiotherapy system comprising a static radiation source (e.g., photon source (e.g., x-ray source)) comprising a narrow diameter waveguide between the linac electron source and the target and comprising shielding around the target) and a radiation trap, e.g., as shown in FIG. 1.

In some embodiments, methods comprise providing a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein).

In some embodiments, methods comprise providing an integrated radioimaging and/or radiotherapy system (e.g., a mobile system) comprising a static radiation source (e.g., photon source (e.g., x-ray source)) comprising a narrow diameter waveguide between the linac electron source and the target and comprising shielding around the target) and a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein), in some embodiments provided on a mobile platform, e.g., provided on a vehicle such as a bus, van, trailer, truck, or the like.

In some embodiments, methods comprise identifying a patient for imaging and/or for treatment with radiation. In some embodiments, methods comprise selecting a patient for imaging and/or for treatment with radiation. In some embodiments, methods comprise providing a patient. In some embodiments, methods comprises providing a patient between a radiation source (e.g., photon source (e.g., x-ray source)) comprising a narrow diameter waveguide between the linac electron source and the target and comprising shielding around the target) and a radiation trap technology as described herein, e.g., as shown in FIG. 1. In some embodiments, methods comprise rotating a patient. In some embodiments, methods comprise exposing a patient while exposing the patient to radiation.

In some embodiments, methods comprise providing a patient positioning system. In some embodiments, methods comprise placing a patient on a patient positioning system. In some embodiments, methods comprise positioning a patient. In some embodiments, positioning a patient comprises positioning a patient using a patient positioning system. In some embodiments, the patient positioning system is as described in Int'l Pat. App. Pub. No. WO 2019/056055 and U.S. Pat. App. Pub. No. 2020/0268327, each of which is incorporated herein by reference. In some embodiments, methods comprise producing radiation. In some embodiments, methods comprise contacting a patient with radiation. In some embodiments, methods comprise rotating a component of the patient positioning system. In some embodiments, methods comprise rotating a patient using the patient positioning system. In some embodiments, methods comprise rotating a component of the patient positioning system and/or rotating a patient using the patient positioning system while the patient is being exposed to radiation.

In some embodiments, methods comprise contacting a patient, tumor, tissue, cell, and/or organ with radiation; and minimizing and/or eliminating stray radiation using a radiation shielding trap as provided herein. In some embodiments, methods comprise providing radiation for imaging, diagnosis, and/or therapy. In some embodiments, methods comprise providing radiation for curative and/or for adjuvant therapy. In some embodiments, methods comprise providing radiation for palliative care.

Systems

In some embodiments, the technology provides a system for radiation-based imaging and/or therapy comprising a radiation source (e.g., photon source (e.g., x-ray source)) comprising a narrow diameter waveguide between the linac electron source and the target and comprising shielding around the target) and a radiation trap, e.g., an integrated system as described above. In some embodiments, the technology provides an integrated radioimaging and/or radiotherapy system comprising a static radiation source (e.g., photon source (e.g., x-ray source)) comprising a narrow diameter waveguide between the linac electron source and the target and comprising shielding around the target) and a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein).

In some embodiments, the technology provides a mobile system for radiation-based imaging and/or therapy comprising a radiation source (e.g., photon source (e.g., x-ray source)) comprising a narrow diameter waveguide between the linac electron source and the target and comprising shielding around the target) and a radiation trap, e.g., an integrated system as described above, installed on a mobile platform such as a vehicle (e.g., a bus, van, trailer, truck, or the like). In some embodiments, the technology provides a mobile integrated radioimaging and/or radiotherapy system comprising a static radiation source (e.g., photon source (e.g., x-ray source)) comprising a narrow diameter waveguide between the linac electron source and the target and comprising shielding around the target) and a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein); and wherein the static radiation source and radiation trap are installed on a mobile platform such as a vehicle (e.g., a bus, van, trailer, truck, or the like).

In some embodiments, systems (e.g., mobile systems) further comprise a patient positioning system. In some embodiments, the patient positioning system is as described in Int'l Pat. App. Pub. No. WO 2019/056055 and U.S. Pat. App. Pub. No. 2020/0268327, each of which is incorporated herein by reference. Accordingly, in some embodiments, systems (e.g., mobile systems) comprise a static radiation source (e.g., photon source (e.g., x-ray source)) comprising a narrow diameter waveguide between the linac electron source and the target and comprising shielding around the target), a patient positioning system (e.g., as described in Int'l Pat. App. Pub. No. WO 2019/056055 and U.S. Pat. App. Pub. No. 2020/0268327, each of which is incorporated herein by reference), and a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein); and wherein, in some embodiments, the static radiation source (e.g., photon source (e.g., x-ray source)) comprising a narrow diameter waveguide between the linac electron source and the target and comprising shielding around the target), patient positioning system, and/or radiation trap are installed on a mobile platform such as a vehicle (e.g., a bus, van, trailer, truck, or the like).

In some embodiments, systems (e.g., mobile systems) comprise a source that produces electromagnetic radiation (e.g., ionizing radiation). In some embodiments, the source is a linear accelerator (abbreviated "linac") that produces x-rays. In some embodiments, the source is a linac that produces photons. In some embodiments, the source is a photon source (e.g., x-ray source)) comprising a narrow diameter waveguide between the linac electron source and the target and comprising shielding around the target, e.g., as described herein.

For example, in some embodiments, the technology provides systems (e.g., mobile systems) comprising a radiation trap and a photon source (e.g., photon source (e.g., x-ray source)) comprising a narrow diameter waveguide between the linac electron source and the target and comprising shielding around the target) having an energy within the energy range typically used for treatment of a patient with a photon beam, e.g., approximately 4 to 25 MeV (e.g., approximately 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 MeV), in some embodiments installed on a mobile platform such as a vehicle (e.g., a bus, van, trailer, truck, or the like). In some embodiments, the technology provides systems (e.g., mobile systems) comprising a radiation trap and an x-ray source (e.g., an x-ray source comprising a narrow diameter waveguide between the linac electron source and the target and comprising shielding around the target) having an energy within the energy range typically used for treatment of a patient with an x-ray beam, e.g., approximately 6 MV (e.g., approximately 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 MV)), in some embodiments installed on a mobile platform such as a vehicle (e.g., a bus, van, trailer, truck, or the like). In some embodiments, the technology provides a system (e.g., a mobile system) comprising a radiation trap and a photon source (e.g., e.g., x-ray source) comprising a narrow diameter waveguide between the linac electron source and the target and comprising shielding around the target) having an energy within the energy range typically used for imaging a patient with a photon source (e.g., x-ray source), e.g., approximately 40 to 150 kV (e.g., approximately 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 kV), in some embodiments installed on a mobile platform such as a vehicle (e.g., a bus, van, trailer, truck, or the like).

In some embodiments, systems further comprise radiation sensors to detect radiation and provide alerts describing stray radiation levels.

In some embodiments, systems comprise a treatment room comprising an integrated radioimaging and/or radiotherapy system comprising a static radiation source (e.g., photon source (e.g., x-ray source)) comprising a narrow diameter waveguide between the linac electron source and the target and comprising shielding around the target) and a radiation shielding trap (e.g., as described hereinabove). In some embodiments, systems comprise a mobile platform (e.g., a vehicle (e.g., a bus, van, trailer, truck, or the like)) comprising the integrated radioimaging and/or radiotherapy system comprising a static radiation source (e.g., photon source (e.g., x-ray source)) comprising a narrow diameter waveguide between the linac electron source and the target and comprising shielding around the target) and a shielding trap (e.g., as described hereinabove). In some embodiments, systems comprise a treatment room comprising a static radiation source (e.g., photon source (e.g., x-ray source)) comprising a narrow diameter waveguide between the linac electron source and the target and comprising shielding around the target), a patient positioning system (e.g., as described in Int'l Pat. App. Pub. No. WO 2019/056055 and U.S. Pat. App. Pub. No. 2020/0268327, each of which is incorporated herein by reference), and a shielding trap comprising a second barrier, a chamber, and a first barrier comprising a window that comprises a material that allows radiation to pass into the trap but not out of the trap (e.g., as described hereinabove). In some embodiments, systems comprise a mobile platform (e.g., a vehicle (e.g., a bus, van, trailer, truck, or the like)) comprising a static radiation source (e.g., photon source (e.g., x-ray source)) comprising a narrow diameter waveguide between the linac electron source and the target and comprising shielding around the target), a patient positioning system (e.g., as described in Int'l Pat. App. Pub. No. WO 2019/056055 and U.S. Pat. App. Pub. No. 2020/0268327, each of which is incorporated herein by reference), and a shielding trap comprising a second barrier, a chamber, and a first barrier comprising a window that comprises a material that allows radiation to pass into the trap but not out of the trap (e.g., as described hereinabove).

In some embodiments, systems (e.g., mobile systems) further comprise radiation sensors to detect radiation and provide alerts describing stray radiation levels.

In some embodiments, systems (e.g., mobile systems) comprise a treatment room comprising an integrated radioimaging and/or radiotherapy system comprising a static radiation source (e.g., photon source (e.g., x-ray source)) comprising a narrow diameter waveguide between the linac electron source and the target and comprising shielding around the target) and a radiation trap (e.g., as described hereinabove). In some embodiments, systems comprise a mobile platform (e.g., a vehicle (e.g., a bus, van, trailer, truck, or the like)) comprising the integrated radioimaging and/or radiotherapy system comprising a static radiation source and a radiation trap (e.g., as described hereinabove). In some embodiments, systems comprise a treatment room comprising a static radiation source, a patient positioning system (e.g., as described in Int'l Pat. App. Pub. No. WO 2019/056055 and U.S. Pat. App. Pub. No. 2020/0268327, each of which is incorporated herein by reference), and a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein); and wherein, in some embodiments, the static radiation source, treatment room, patient positioning system, and/or radiation trap are installed on a mobile platform such as a vehicle (e.g., a bus, van, trailer, truck, or the like).

In some embodiments, systems comprise a mobile platform (e.g., a vehicle (e.g., a bus, van, trailer, truck, or the like)) comprising a static radiation source (e.g., photon source (e.g., x-ray source)) comprising a narrow diameter waveguide between the linac electron source and the target and comprising shielding around the target), a patient positioning system (e.g., as described in Int'l Pat. App. Pub. No. WO 2019/056055 and U.S. Pat. App. Pub. No. 2020/0268327, each of which is incorporated herein by reference), a treatment room, and a radiation trap comprising a second barrier, a first barrier, and a chamber, wherein the first barrier comprises a window that maximizes transmission of radiation into the chamber and minimizes transmission of radiation out of the chamber (e.g., minimizes transmission of radiation from the chamber, through the window, and into the treatment room comprising a patient) and wherein the chamber comprises materials arranged in a number of stratified layers arranged parallel to (e.g., substantially and/or essentially parallel to) the window and/or the second barrier and are further arranged to comprise materials having an increasing Z as a function of distance from the window to the second barrier (as described herein).

In some embodiments, systems (e.g., mobile systems) do not comprise a bunker around said system, e.g., in some embodiments, systems are bunker-free (e.g., mobile bunker-free systems).

In some embodiments, systems comprise functionalities for collecting, storing, and/or analyzing data. For example, in some embodiments systems comprises a processor, a memory, and/or a database for, e.g., storing and executing instructions, analyzing data, performing calculations using the data, transforming the data, and storing the data. Moreover, in some embodiments, systems comprise a processor configured to control the source. In some embodiments, the processor is used to initiate and/or terminate production of radiation by the source and/or for data collection. In some embodiments, systems comprise a user interface (e.g., a keyboard, buttons, dials, switches, and the like) for receiving user input that is used by the processor to initiate and/or terminate production of radiation by the source. In some embodiments, systems further comprise a data output for transmitting data to an external destination, e.g., a computer, a display, a network, and/or an external storage medium.

Also provided herein are methods employing any of the systems described herein for radiation therapy and/or radiation-based imaging of a patient. The methods include those processes undertaken by individual participants in the system (e.g., medical service providers, technicians, doctors, patients, etc.) as well as collective activities of one or more participants working in coordination or independently from each other.

Some portions of this description describe the embodiments of the technology in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times to refer to these arrangements of operations as modules, without loss of generality. The described operations and their associated modules may be embodied in software, firmware, hardware, or any combinations thereof.

Certain steps, operations, or processes described herein may be performed or implemented with one or more hardware or software modules, alone or in combination with other devices. In some embodiments, a software module is implemented with a computer program product comprising a computer-readable medium containing computer program code, which can be executed by a computer processor for performing any or all steps, operations, or processes described.

In some embodiments, systems comprise a computer and/or data storage provided virtually (e.g., as a cloud computing resource). In particular embodiments, the technology comprises use of cloud computing to provide a virtual computer system that comprises the components and/or performs the functions of a computer as described herein. Thus, in some embodiments, cloud computing provides infrastructure, applications, and software as described herein through a network and/or over the internet. In some embodiments, computing resources (e.g., data analysis, calculation, data storage, application programs, file storage, etc.) are remotely provided over a network (e.g., the internet and/or a cellular network).

Embodiments of the technology may also relate to an apparatus for performing the operations herein. This apparatus may be specially constructed for the required purposes and/or it may comprise a general-purpose computing device selectively activated or reconfigured by a computer program stored in the computer. Such a computer program may be stored in a non-transitory, tangible computer readable storage medium or any type of media suitable for storing electronic instructions, which may be coupled to a computer system bus. Furthermore, any computing systems referred to in the specification may include a single processor or may be architectures employing multiple processor designs for increased computing capability.

Although the disclosure herein refers to certain illustrated embodiments, it is to be understood that these embodiments are presented by way of example and not by way of limitation.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A system comprising:
    a radiation trap comprising a chamber, said chamber comprising:
        1) a first barrier comprising a window, wherein said window transmits high-energy photon radiation and absorbs and/or scatters low-energy photon radiation; and
        2) a second barrier; and
    a static photon source separated from the chamber by the first barrier and the window.

2. The system of claim 1 further comprising a patient positioning system located between the static photon source and the first barrier and the window.

3. The system of claim 1 further comprising a mobile platform.

4. The system of claim 1, wherein the static photon source comprises a narrow diameter waveguide between a linear accelerator (linac) of the static photon source and a target of the static photon source.

5. The system of claim 1, wherein the static photon source produces a beam of 4 to 25 MeV or 40 to 150 kV.

6. The system of claim 1, wherein the system is a mobile bunker-free system.

7. The system of claim 1, further comprising a treatment room comprising said static photon source.

8. The system of claim 1, wherein:
    the first barrier and the second barrier are parallel or substantially parallel;
    the first barrier is closer to a radiation source than the second barrier; and
    the first barrier and the second barrier are positioned on opposing sides of the chamber.

9. The system of claim 1, wherein the radiation trap further comprises a lateral wall.

10. The system of claim 1, wherein said chamber comprises materials that absorb and/or scatter radiation within the chamber.

11. The system of claim 1, wherein said chamber comprises materials having a Z that is less than the Z of the second and/or first barrier.

12. The system of claim 1, wherein said second barrier and/or said first barrier comprise a high-density material.

13. The system of claim 1, wherein said second barrier and/or said first barrier comprise lead.

14. The system of claim 1, wherein said window comprises carbon, copper or aluminum.

15. The system of claim 1, wherein the first barrier is approximately 30 cm thick or approximately 20 cm thick.

16. The system of claim 1, wherein the second barrier is approximately 36 cm thick.

17. The system of claim 1, wherein the second barrier is approximately 60 cm from the first barrier.

18. The system of claim 1, wherein the window is approximately 1-50 mm thick.

19. The system of claim 1, wherein the chamber comprises materials arranged in a number of stratified layers arranged substantially parallel to the window and/or the second barrier.

20. The system of claim 1, wherein the system is a therapy system or an imaging system.

21. The system of claim 1, wherein the static photon source provides a photon radiation beam.

22. The system of claim 1, wherein the window transmits high-energy photon radiation contacting the window on a first side of the window and absorbs and/or scatters low-energy photon radiation contacting the window on a second side of the window.

23. The system of claim 1, wherein the chamber comprises air.

24. The system of claim 2, wherein the patient positioning system is configured to rotate a patient.

25. The system of claim 2, wherein the static photon source is oriented to provide a photon radiation beam toward the patient positioning system and toward the chamber.

26. The system of claim 20, wherein the mobile platform is a bus, van, trailer, or truck.

27. The system of claim 4, wherein the static photon source comprises shielding around the target.

28. The system of claim 9, wherein said lateral wall comprises a high-density material.

29. The system of claim 9, wherein said lateral wall comprises lead.

30. The system of claim 19, wherein the stratified layers are arranged to have an increasing Z as a function of distance from the window to the second barrier.

\* \* \* \* \*

UNITED STATES PATENT AND TRADEMARK OFFICE
CERTIFICATE OF CORRECTION

Page 1 of 1

PATENT NO. : 12,042,313 B2
APPLICATION NO. : 17/680798
DATED : July 23, 2024
INVENTOR(S) : Mark Strangeman et al.

It is certified that error appears in the above-identified patent and that said Letters Patent is hereby corrected as shown below:

In the Claims

Claim 26, Column 35, Line 11 reads:
"26. The system of claim 20, wherein the mobile platform",
Whereas it should read:
"26. The system of claim 3, wherein the mobile platform".

Signed and Sealed this
Twenty-second Day of October, 2024

Katherine Kelly Vidal
*Director of the United States Patent and Trademark Office*